US010751378B2

(12) United States Patent
Oh et al.

(10) Patent No.: US 10,751,378 B2
(45) Date of Patent: Aug. 25, 2020

(54) **PHARMACEUTICAL COMPOSITION COMPRISING *PISTACIA WEINMANNIFOLIA* EXTRACT, FRACTION OF SAME OR COMPOUND SEPARATED FROM SAME FOR PREVENTING OR TREATING CHRONIC OBSTRUCTIVE PULMONARY DISEASE (COPD)**

(71) Applicant: Korea Research Institute of Bioscience and Biotechnology, Daejeon (KR)

(72) Inventors: Sei Ryang Oh, Daejeon (KR); Kyung Seop Ahn, Daejeon (KR); Seung Hyung Kim, Daejeon (KR); In Sik Shin, Daejeon (KR); Hang Jin, Yunnan (CN); Jung Hee Kim, Daejeon (KR); Hyung Won Ryu, Daejeon (KR); Wan Yi Li, Yunnan (CN); Sang Woo Lee, Daejeon (KR); Joong Ku Lee, Daejeon (KR); Sang Ho Choi, Daejeon (KR)

(73) Assignee: KOREA RESEARCH INSTITUTE OF BIOSCIENCE AND BIOTECHNOLOGY (KR)

(*) Notice: Subject to any disclaimer, the term of this patent is extended or adjusted under 35 U.S.C. 154(b) by 637 days.

(21) Appl. No.: 15/304,316

(22) PCT Filed: Apr. 17, 2015

(86) PCT No.: PCT/KR2015/003881
§ 371 (c)(1),
(2) Date: Oct. 14, 2016

(87) PCT Pub. No.: WO2015/160219
PCT Pub. Date: Oct. 22, 2015

(65) Prior Publication Data
US 2017/0035822 A1 Feb. 9, 2017

(30) Foreign Application Priority Data
Apr. 17, 2014 (KR) .................. 10-2014-0046105

(51) Int. Cl.
| | |
|---|---|
| *A61K 36/22* | (2006.01) |
| *A23L 33/105* | (2016.01) |
| *A61K 9/00* | (2006.01) |
| *A61K 31/12* | (2006.01) |
| *A61P 11/00* | (2006.01) |

(52) U.S. Cl.
CPC ............ *A61K 36/22* (2013.01); *A23L 33/105* (2016.08); *A61K 9/0053* (2013.01); *A61K 31/12* (2013.01); *A23V 2002/00* (2013.01); *A61K 2236/33* (2013.01); *A61P 11/00* (2018.01)

(58) Field of Classification Search
CPC .............. A23L 33/105; A23V 2002/00; A61K 2236/33; A61K 31/12; A61K 36/22; A61K 9/0053; A61P 11/00; A61P 11/08; A61P 25/00; A61P 25/28; A61P 29/00; A61P 43/00
See application file for complete search history.

(56) References Cited

FOREIGN PATENT DOCUMENTS

| | | |
|---|---|---|
| CN | 105705155 A | 6/2016 |
| EP | 2 559 434 A2 | 2/2013 |
| EP | 3 025 721 A1 | 6/2016 |
| JP | 2004-262905 A | 9/2004 |
| JP | 2017-506239 A | 3/2017 |
| WO | WO 2015/124934 A1 | 8/2015 |

OTHER PUBLICATIONS

Hisatoshi et al. (2000) "Fenspiride," 呼吸 [Respiration]. 19(2)159-162.—Chemical Structures Only.
Minami et al. (2006) "Isolation and identification of histamine-release inhibitors from Pistacia weinmannifolia J. Pisson ex. Franch," Journal of Natural Medicines. 60:138-140.
Shirole et al. (May 14, 2014) "Investigation into the mechanism of action of essential oil of Pistacia integerrima for its antiasthmatic activity," J. Ethnopharmacol. 153:541-551.
Office Action corresponding to Japanese Patent Application No. 2017-506239, dispatched Jul. 31, 2017—Search results on p. 5 only.
Search Report corresponding to European Patent Application No. 15779202.9, dated Nov. 2, 2017.
Carvalho et al. (2004) "Luxenchalcone, a New Bichalcone and other Constituents from Luxemburgia octandra," J. Braz. Chem. Soc. 15(1):146-149.
Buenestado et al. (Jun. 13, 2013) "Response to commentary: 'If roflumilast inhibits the innate immunity in the stable patient, what about infection?'" The Clinical Respiratory Journal. 7(3):e20-e21.

(Continued)

*Primary Examiner* — Aaron J Kosar
(74) *Attorney, Agent, or Firm* — Lathrop GPM LLP; Andrew T. Wilkins; Michael J. Spellberg

(57) ABSTRACT

The present invention relates to a composition for suppressing chronic obstructive pulmonary disease (COPD) comprising a *Pistacia weinmannifolia* extract, a fraction thereof, or a compound isolated therefrom and, more particularly, to a pharmaceutical composition for preventing or treating COPD comprising a *Pistacia weinmannifolia* extract, a fraction thereof, or a compound isolated therefrom; a food composition for preventing or improving COPD, and the compound isolated therefrom. The composition comprising a *Pistacia weinmannifolia* extract, a fraction thereof, or a compound isolated therefrom, according to the present invention, is not toxic, suppresses the invasion of inflammatory cells into the bronchial tube of a COPD-induced animal model, and effectively suppresses the expression of CXCL-1, TNF-α, or MIP-2. In addition, due to the use of a safety-proven herbal drug as a raw material, the composition of the present invention can resolve various side-effects of existing therapeutic agents for COPD, chronic obstructive bronchitis, chronic bronchiolitis, emphysema, multiple sclerosis, and acute and chronic inflammation, and thus can be effectively used as a composition for preventing, treating and remedying COPD.

18 Claims, 9 Drawing Sheets

(56) References Cited

OTHER PUBLICATIONS

Curtis et al. (2007) "The Immunopathogenesis of Chronic Obstructive Pulmonary Disease," Proceedings of the American Thoracic Society. 4(7):512-521.
Lomas-Neira et al. (2005) "Divergent roles of murine neutrophil chemokines in hemorrhage induced priming for acute lung injury," 31(3):169-179.
Mdee et al. (2003) "Rhuschalcones II-VI, Five New Bichalcones from the Root Bark of Rhus pyroides," J. Nat. Prod. 66(5):599-604.
Minami et al. (2005) "Isolation and identification of histamine-release inhibitors from Pistacia weinmannifolia J. Pisson ex. Franch," Journal of Natural Medicines. 60(2):138-140.
Nikota et al. (2011) "A mouse GM-CSF receptor antibody attenuates neutrophilia in mice exposed to cigarette smoke," =Eur. Respir. J. 38:285-294.
Nikota et al. (2011) "Differential expression and function of breast regression protein 39 (BRP-39) in murine models of subacute cigarette smoke exposure and allergic airway inflammation," Respiratory Research. 12:39. pp. 1-12.
Qin et al. (2011) "Epigallocatechin-3-Gallate Reduces Airway Inflammation in Mice through Binding to Proinflammatory Chemokines and Inhibiting Inflammatory Cell Recruitment," J. Immunol. 186(6):3693-3700.
Rahman (Nov. 9, 2011) "Pharmacological antioxidant strategies as therapeutic interventions for COPD," Biochim. Biophys. Acta. 1822(5):714-728.
Zhao et al. (2005) "Antioxidant properties of two gallotannins isolated from the leaves of Pistacia weinmannifolia," Biochim Biophys Acta. 1725:103-110.
International Search Report corresponding to International Patent Application No. PCT/KR2015/003881, dated Jul. 29, 2015.

[FIG. 1]
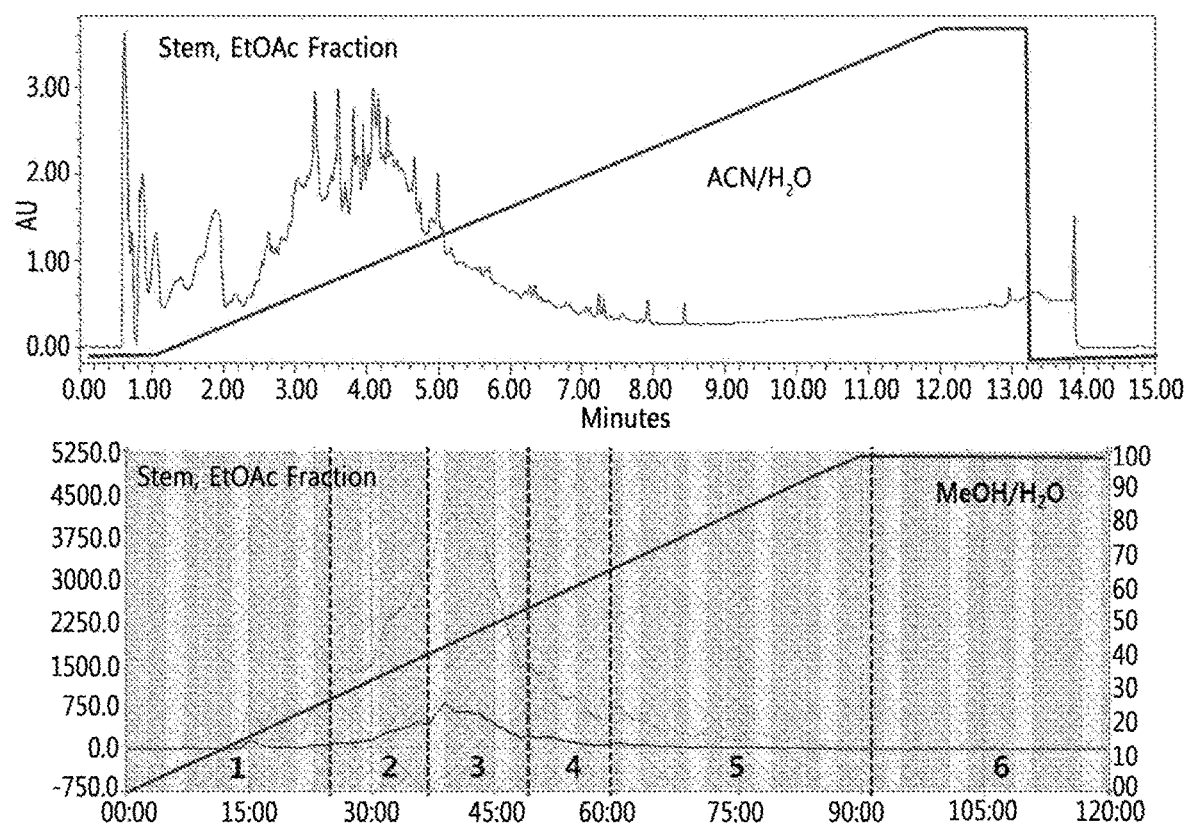

[FIG. 2]
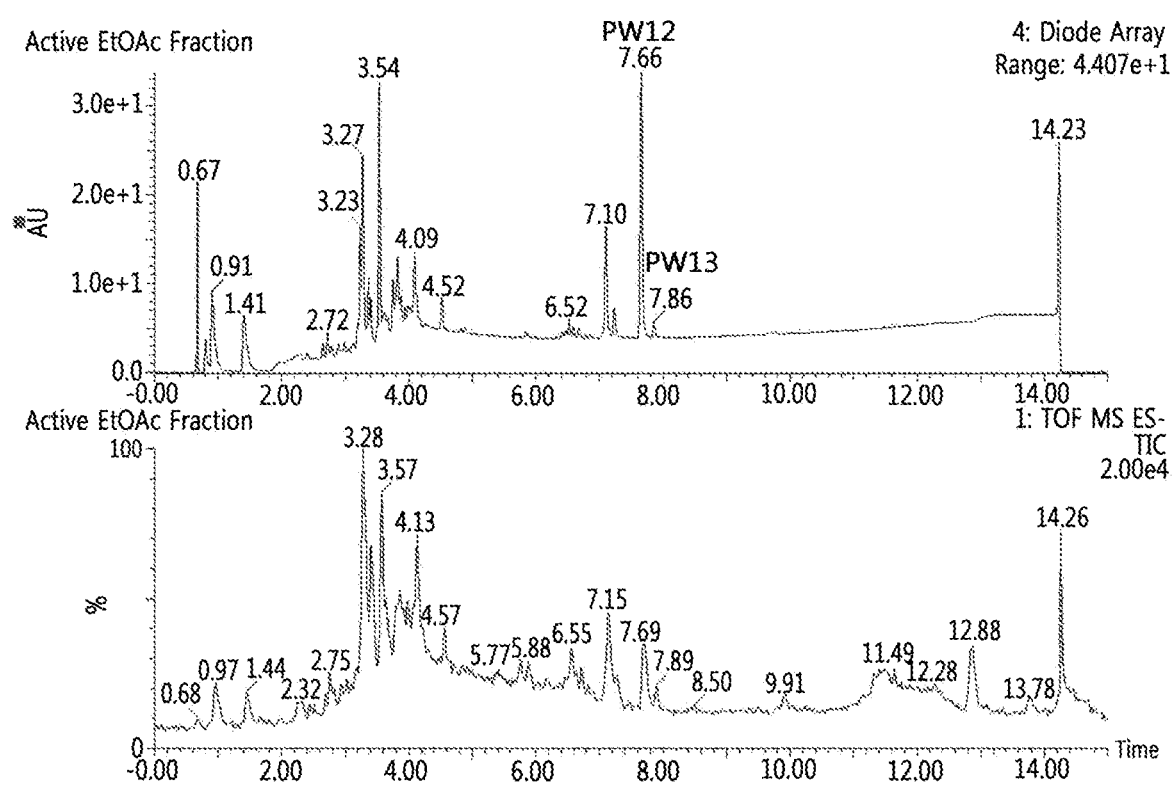

[FIG. 3A]
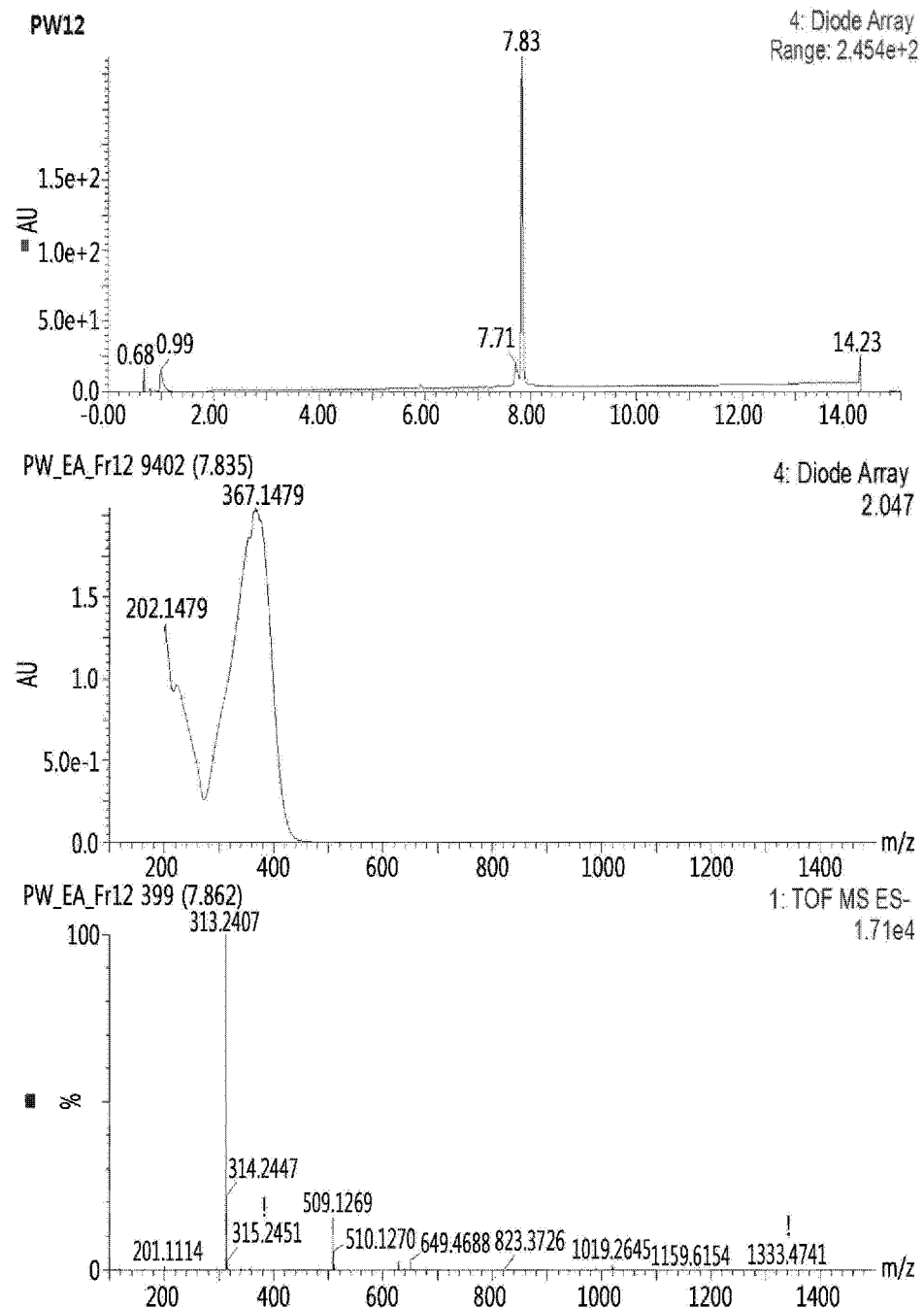

[FIG. 3B]
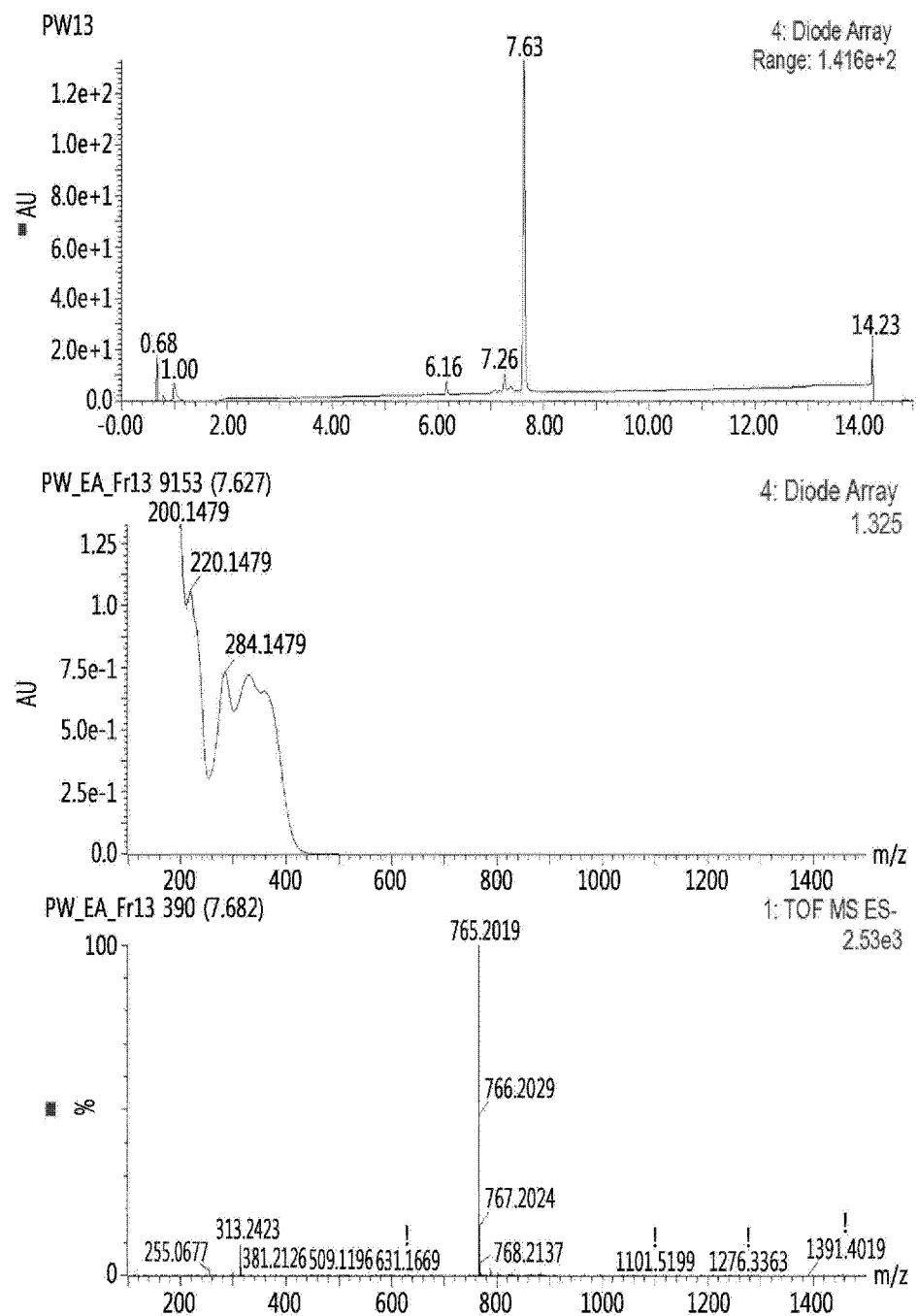

[FIG. 4A]
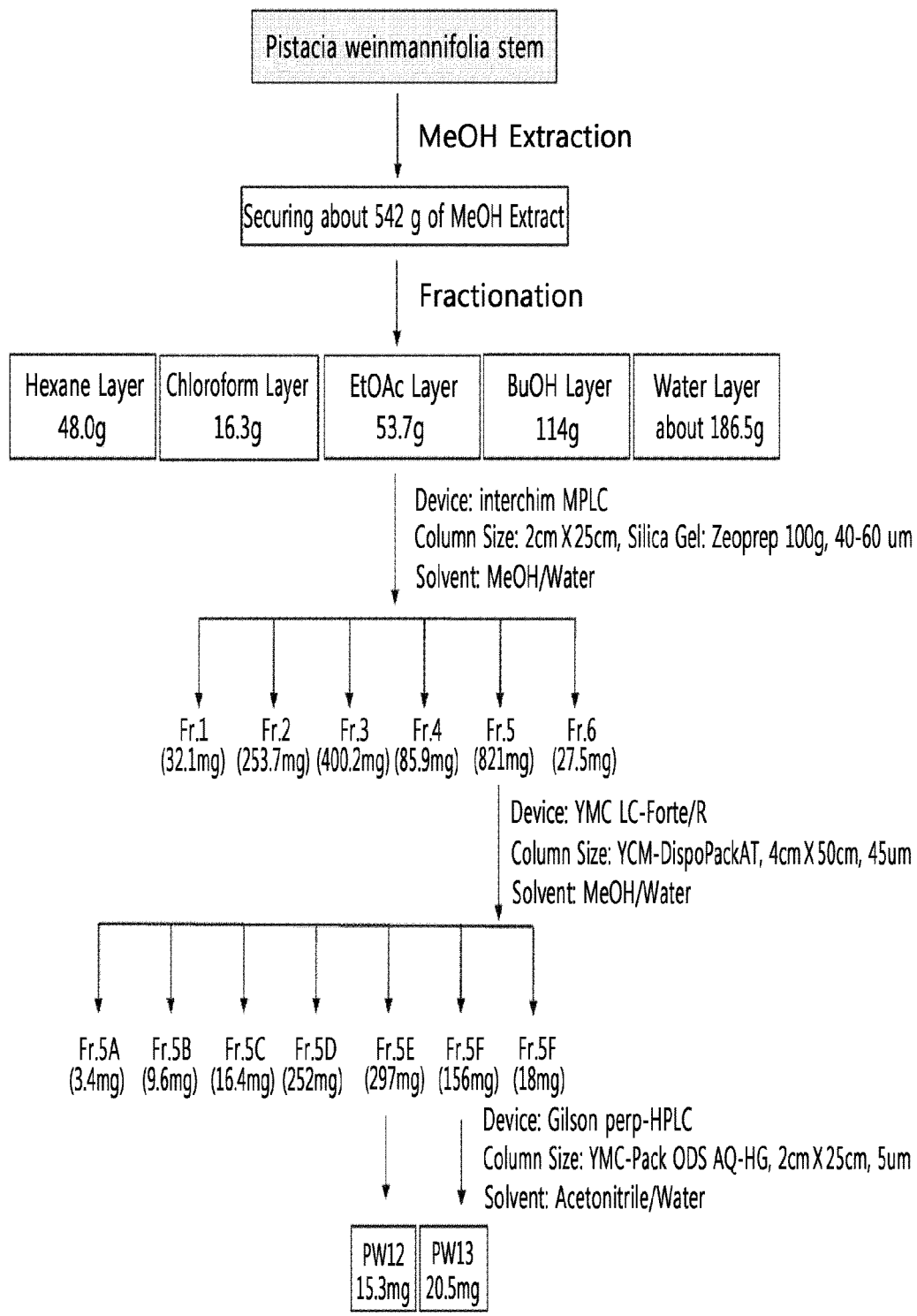

[FIG. 4B]
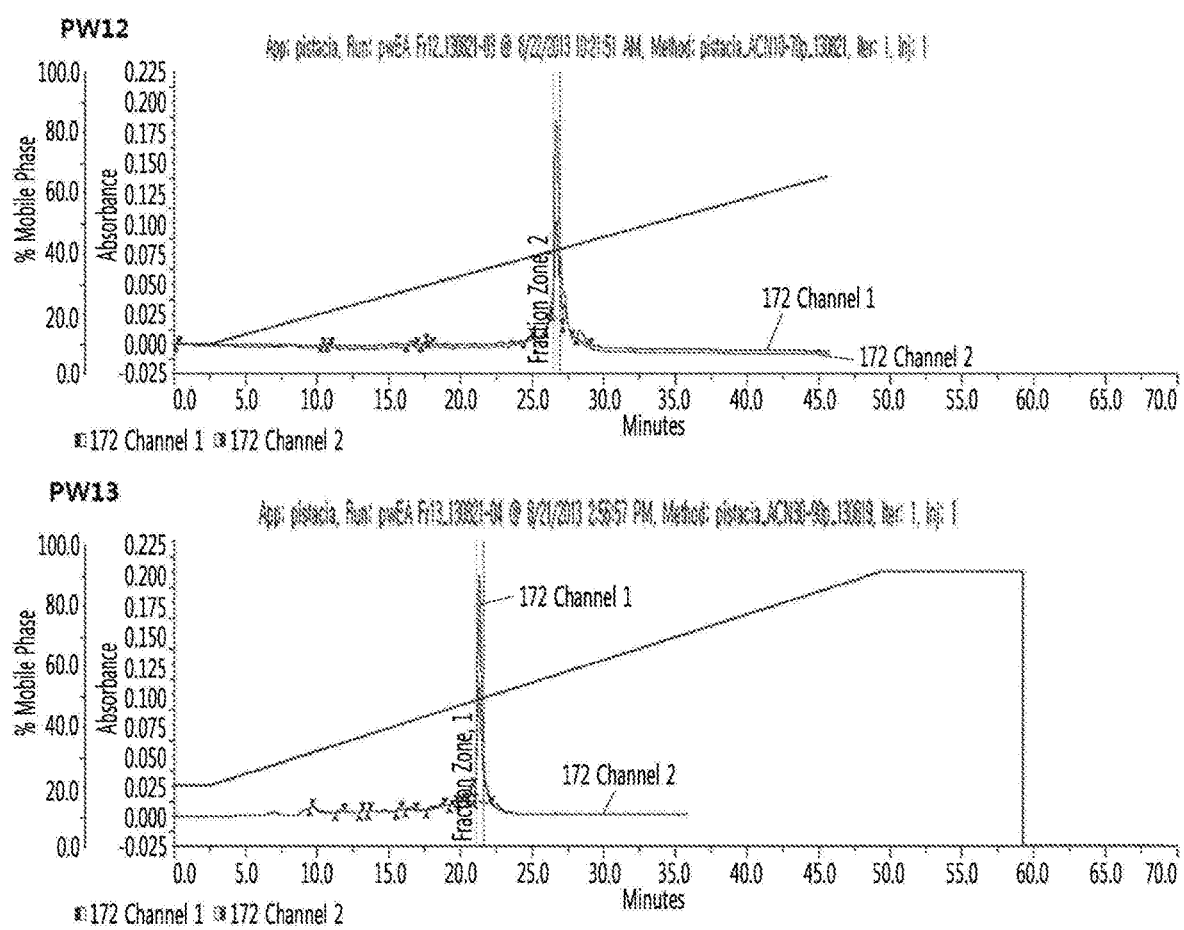

[FIG. 5]
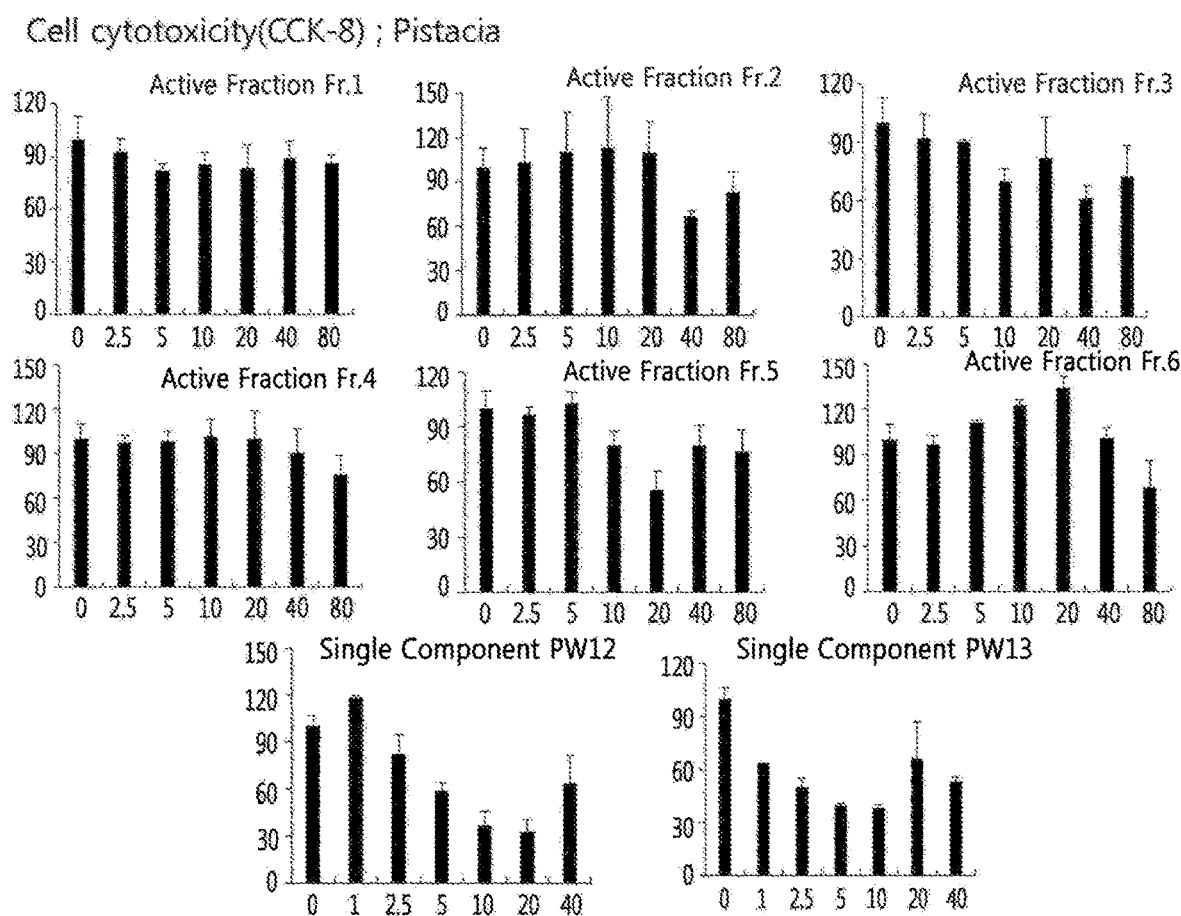

[FIG. 6]
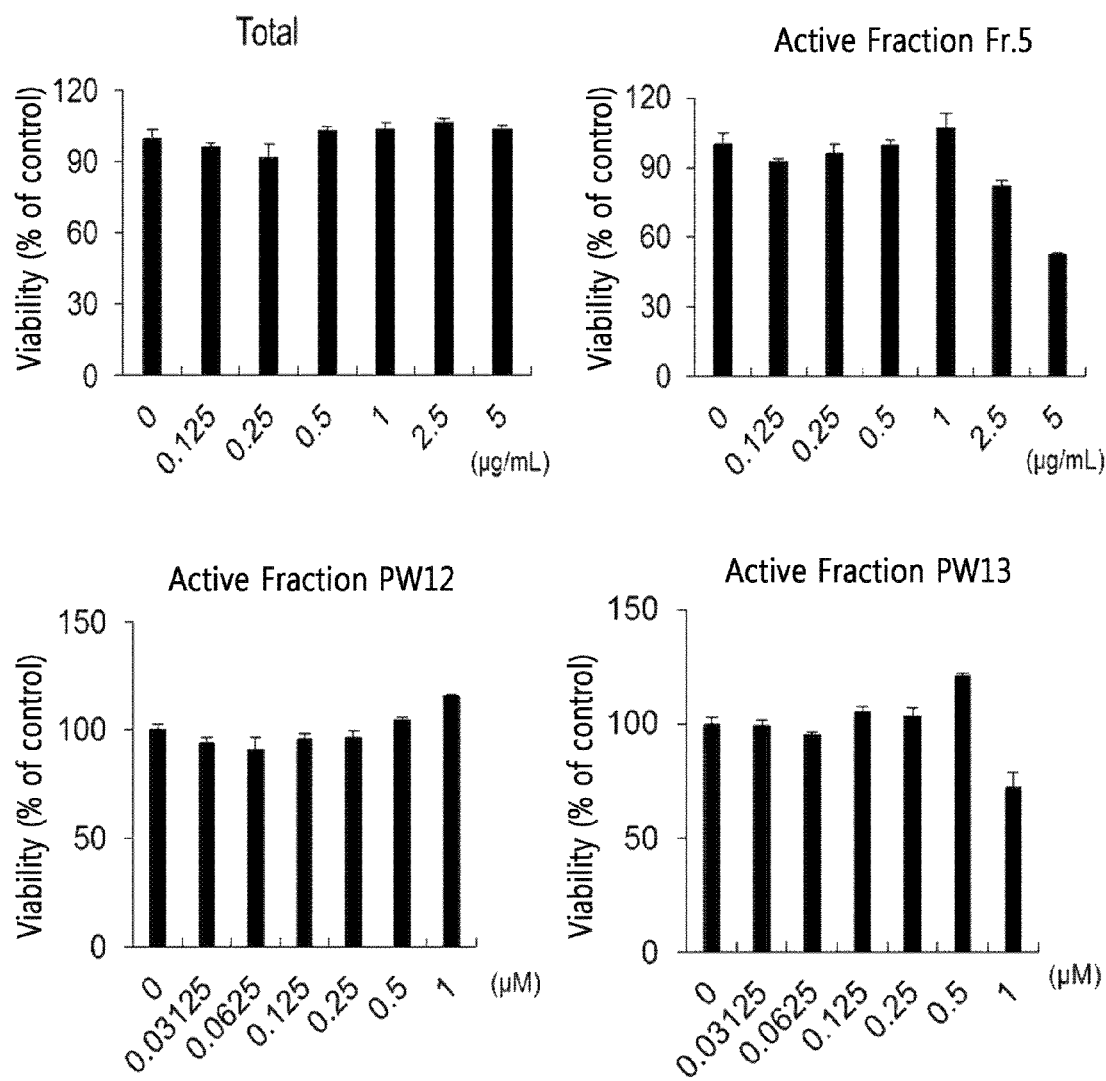

[FIG. 7]
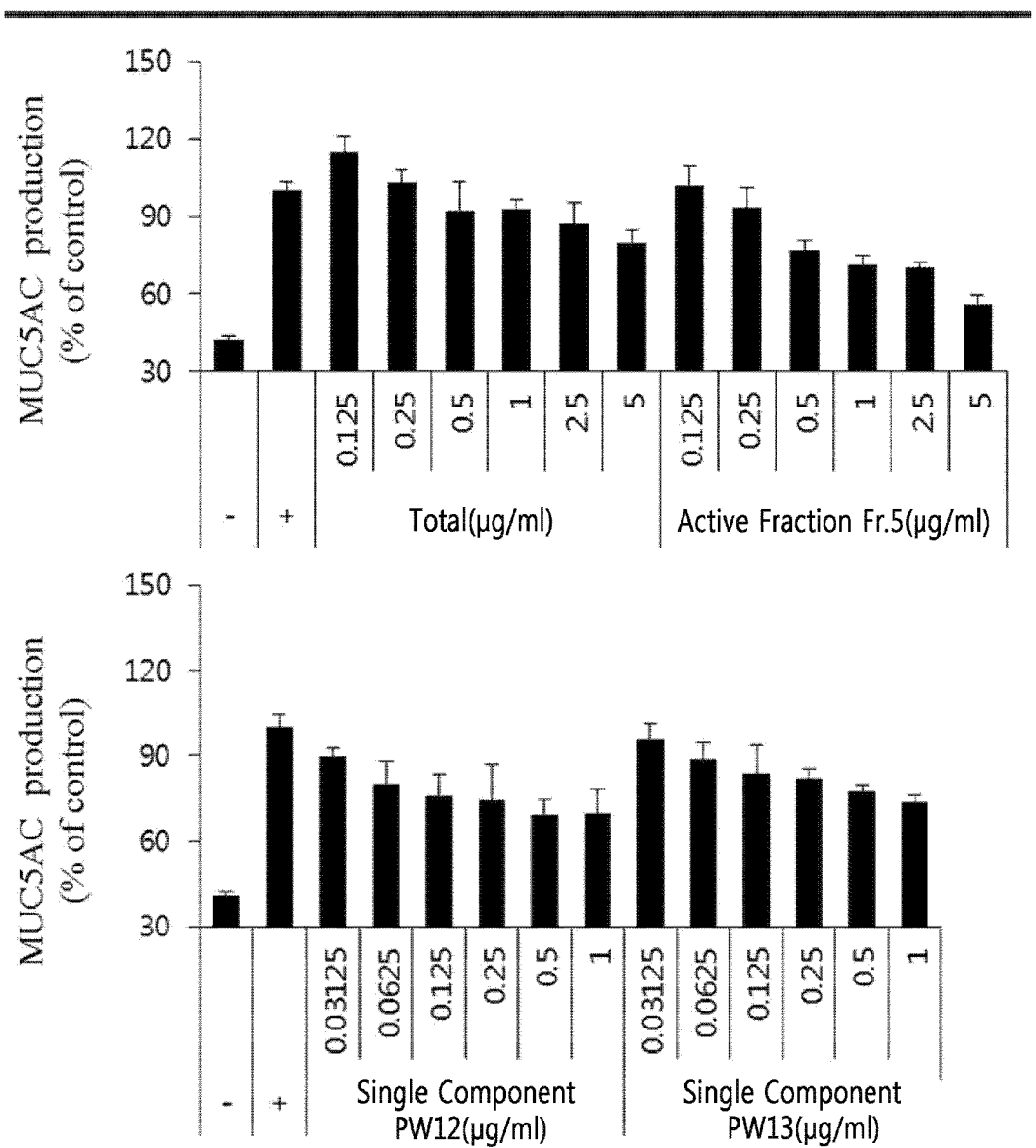

PHARMACEUTICAL COMPOSITION COMPRISING *PISTACIA WEINMANNIFOLIA* EXTRACT, FRACTION OF SAME OR COMPOUND SEPARATED FROM SAME FOR PREVENTING OR TREATING CHRONIC OBSTRUCTIVE PULMONARY DISEASE (COPD)

RELATED APPLICATIONS

This application is a 35 U.S.C. § 371 filing of International Application No. PCT/KR2015/003881, filed Apr. 17, 2015, which claims priority to Korean Patent Application No. 10-2014-0046105, filed Apr. 17, 2014, each of which is incorporated herein by reference in their entireties.

TECHNICAL FIELD

The present invention relates to a composition for suppressing chronic obstructive pulmonary disease (COPD) comprising a *Pistacia weinmannifolia* extract, a fraction thereof, or a compound isolated therefrom and, more particularly, to a pharmaceutical composition for preventing or treating COPD comprising a *Pistacia weinmannifolia* extract, a fraction thereof, or a compound isolated therefrom; a food composition for preventing or improving COPD, and the compound isolated therefrom.

BACKGROUND ART

Chronic obstructive pulmonary disease (COPD, hereinafter), one of the representative lung diseases along with asthma, differs from asthma in that it accompanies an irreversible airway obstruction. COPD is an important disease which is currently ranked as the fourth leading cause of death in the world and shows a unique increase in its occurrence among the top ten diseases. COPD is a disease that occurs due to pathological changes in the bronchioles and lung parenchyma, which are caused by infections in the airway and lung parenchyma, and it is characterized by having obstructive bronchiolitis and emphysema (destruction of lung parenchyma). The types of COPD include chronic obstructive bronchitis, chronic bronchiolitis, and emphysema. The primary risk factor of COPD is thought to be cigarette smoking. Smoke acts as a strong toxic material in the lung tissue and causes promotion of the generation of oxidized materials, proinflammatory factors, and chemotactic factors, thereby promoting excessive transport of inflammatory cells such as neutrophils. The inflammatory cells transported to the inside of the lung tissue also secrete many inflammatory mediators, thus worsening the inflammation in the lung tissue. Examples of the well-known inflammatory mediators may include TNF-α, MIP-1, CXCL-1, etc., and they are used as important markers in inflammatory responses due to cigarette smoke.

The therapeutic materials used for treating COPD have been developed to improve the inflammation in the lung tissue, and they are mainly steroids, anti-inflammatory agents, etc. However, these therapeutic materials can cause various side-effects such as immunosuppression and resistance, and thus they are not suitable for the COPD patients who require long-term treatment.

Until now, in the case of COPD such as asthma, therapeutic agents having the effects of anti-inflammation or bronchodilation have mostly been used for the treatment of inflammation. However, a significant number of these conventional therapeutic agents require caution due to many side-effects. Examples of the representative therapeutic agents may include glucocorticoid, leukotriene modifiers, theophylline, etc. In the case of glucocorticoids, they have a strong effect but also have a problem in that they suppress all immune responses and anti-inflammatory responses including even the necessary immune responses instead of acting selectively, and thus there is an issue of drug side-effects and they are thus used for inhalation treatment. In the case of leukotriene modifiers, they have few side-effects but, due to the limited effects, they cannot control asthma when used alone, and thus they are mostly used as a subordinate agent. In the case of theophyllines, they have problems in that they do not have excellent effect and there is also a risk of side-effects. In the case of corticosteroids, they have an excellent therapeutic effect, but, under the long-term treatment, they are known to induce adrenal suppression, decrease of bone density, growth disorder, complications in the eyes and skin, increase of collagen synthesis, etc. in proportion to the dosage and duration of administration. In the case of long-acting β2 agonists such as salmeterol and formeterol, they exhibit a preventative effect against convulsions but they have been warned against because they may cause death of patients under certain conditions. Due to the various side-effects described above, the conventional therapeutic agents for treating inflammation require careful considerations in their use, and thus there is a need for the development of a therapeutic agent having an excellent effect with few side-effects. For this purpose, an accurate understanding of the mechanism of COPD is necessary.

Until now, the exact mechanism of COPD has been almost unknown, and there has been no therapeutic agent that can fundamentally treat the occurrence and progress of COPD, although various treatments have been attempted. Accordingly, studies on the pathogenesis of COPD and development of a fundamental therapeutic agent thereof based on the same are urgently required.

Nevertheless, a recent report related to the study of COPD revealed that chemotactic factors such as MIP-2 and CXCL-1, which promote the transport of inflammatory cells, have an important role in the occurrence and development of COPD (Lomas-Neira et al., 2005; Moriyama et al., 2010). In the progress of COPD, chemokines such as MIP-2 and CXCL-1 exhibit chemotactic effects via conjugation with the receptors of airway epithelial cells, pneumocytes, and inflammatory cells and induce an excessive infiltration of inflammatory cells into the inflammatory area in the lung tissue. Additionally, chemokines activate inflammatory cells, thereby producing proinflammatory factors such as TNF-α, IL-1β, IL-6, and IL-8. Specifically, in the case of TNF-α, it activates an inflammatory signaling system such as NF-κB and MAPK, thereby worsening the inflammatory responses. Additionally, chemokines not only produce proinflammatory factors but also produce various growth factors and reactive oxygen species, which cause sustained inflammation responses, damage in the lung parenchyma tissue, and fibrogenesis in the lung tissue (Lo et al., 2013). Due to a series of these reactions, deterioration in the pulmonary function, which is the most distinctive characteristic of COPD patients, is caused. Accordingly, the inhibition of chemokine production is thought to be a very important method for treating COPD. In fact, many researchers have made efforts to develop therapeutic materials for treating COPD with their studies being focused on the inhibition of chemokines (Buenestado et al., 2013).

Meanwhile, *Pistacia weinmannifolia* J. Poiss, Ex Franch is a plant widely cultivated near the Yunnan Province of China, and it has been used for treating shigellosis, gastroenteritis, flu, and headache since ancient times. According to a previous report, two compounds isolated from the plant were shown to have the ability to remove free oxygen radicals (Zhao X. et al., *Biochim Biophys Acta*, 1725, 103-110, 2005). However, except for the above report, the effect of *Pistacia weinmannifolia* extract, a fraction thereof, or a compound isolated therefrom with respect to the treatment or prevention of COPD has not been known.

DISCLOSURE

Technical Problem

Under the circumstances, the present inventors have made efforts to discover a natural material effective for the treatment of COPD without inducing side-effects in the human body, and as a result, they have confirmed that a *Pistacia weinmannifolia* extract, a fraction thereof, and a compound isolated therefrom can inhibit the number of neutrophils in a COPD-induced mouse model, reduce $CD^{4+}$ in the bronchoalveolar lavage fluid and the number of neutrophils $Gr-1^+$, and inhibit the production of CXCL-1 without showing any toxicity. Additionally, the present inventors have confirmed that the *Pistacia weinmannifolia* extract, a fraction thereof, and a compound isolated therefrom have the effects of reducing the inflammatory cells and amount thereof in the TNF-α in the bronchoalveolar lavage fluid and also reduce MIP-2 and thus can be effectively used for preventing or treating COPD, thereby completing the present invention.

Technical Solution

An object of the present invention is to provide a pharmaceutical composition for preventing or treating COPD containing a *Pistacia weinmannifolia* extract, a fraction thereof, or a compound isolated therefrom as an active ingredient.

Another object of the present invention is to provide a sitological composition for preventing or improving COPD containing a *Pistacia weinmannifolia* extract, a fraction thereof, or a compound isolated therefrom as an active ingredient.

Still another object of the present invention is to provide a compound isolated from *Pistacia weinmannifolia*.

Still another object of the present invention is to provide a method for preventing or treating COPD including administering the pharmaceutical composition to a subject having or being at risk for developing COPD.

Still another object of the present invention is to provide the use of a *Pistacia weinmannifolia* extract, a fraction thereof, or a compound isolated therefrom for preventing or treating COPD.

Advantageous Effects of the Invention

The composition containing a *Pistacia weinmannifolia* extract, a fraction thereof, or a compound isolated therefrom, according to the present invention, is not toxic, suppresses the infiltration of inflammatory cells into the bronchial tube of a COPD-induced animal model, and effectively suppresses the expression of CXCL-1, TNF-α, or MIP-2. In addition, due to the use of a safety-proven herbal drug as a raw material, the composition of the present invention can resolve various side-effects of existing therapeutic agents for COPD, chronic obstructive bronchitis, chronic bronchiolitis, emphysema, multiple sclerosis, and acute and chronic inflammation, and thus can be effectively used as a composition for preventing, treating, and improving COPD.

BRIEF DESCRIPTION OF THE DRAWINGS

FIG. 1 shows the results of isolating an active fraction from a *Pistacia weinmannifolia* extract of using a methanol/water solvent.

FIG. 2 shows the results of UPLC-PDA-QTOF-MS analysis with respect to the active ethyl acetate (EtOAc) fraction of *Pistacia weinmannifolia*.

FIG. 3A shows the results of UPLC-PDA-QTOF-MS analysis with respect to pistachalcone (PW12), a compound isolated from the active fraction of *Pistacia weinmannifolia*.

FIG. 3B shows the results of UPLC-PDA-QTOF-MS analysis with respect to pistachalcone B (PW13), a compound isolated from the active fraction of *Pistacia weinmannifolia*.

FIG. 4A shows a schematic diagram illustrating the process of preparing a methanol extract, a hexane fraction, a chloroform fraction, an ethyl acetate fraction, a butanol fraction, and a water fraction and isolating novel compounds, i.e., pistachalcone (PW12) and pistachalcone B (PW13), from the active ethyl acetate fraction.

FIG. 4B shows the analysis results of fractions for obtaining novel compounds, i.e., pistachalcone (PW12) and pistachalcone B (PW13), at wavelengths of UV 254 nm and 280 nm after the fractionation of the active fraction with an acetonitrile/water solvent.

FIG. 5 shows the results confirming the toxicity of active fractions 1 to 6 of *Pistacia weinmannifolia* and the isolated compounds of pistachalcone (PW12) and pistachalcone B (PW13).

FIG. 6 shows the results confirming the toxicity of a *Pistacia weinmannifolia* extract, active fraction 5 of *Pistacia weinmannifolia*, and the isolated compounds of pistachalcone (PW12) and pistachalcone B (PW13).

FIG. 7 shows the measurement results of inhibition rates of a *Pistacia weinmannifolia* extract, active fraction 5 of *Pistacia weinmannifolia*, and the isolated compounds of pistachalcone (PW12) and pistachalcone B (PW13) against MUC5AC production, induced by TNF-α. The control group (−) (not treated with TNF-α) and the control group (+) (treated with TNF-α) were confirmed as comparative groups.

BEST MODE

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

In order to achieve the above objects, in an aspect, the present invention provides a pharmaceutical composition for preventing or treating COPD containing a *Pistacia weinmannifolia* extract, a fraction thereof, or a compound isolated therefrom as an active ingredient.

The compound of the present invention may include the compounds represented by Formula 1 or Formula 2 shown below.

[Formula 1]

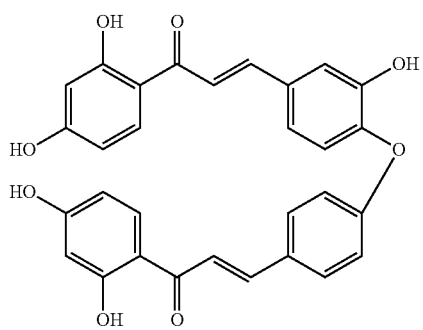

[Formula 2]

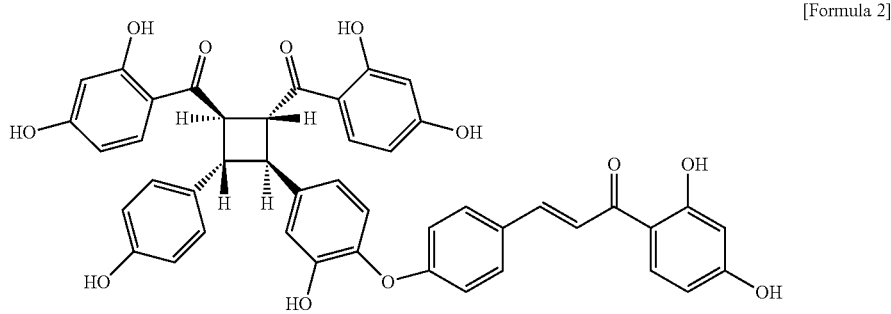

The pharmaceutical composition of the present invention may further include a pharmaceutically acceptable carrier.

COPD differs from asthma in that it accompanies an irreversible airway obstruction. COPD is a disease that occurs due to pathological changes in the bronchioles and lung parenchyma which are caused by infections in the airway and lung parenchyma, and it is characterized by having obstructive bronchiolitis and emphysema (destruction of lung parenchyma). The types of COPD include chronic obstructive bronchitis, chronic bronchiolitis, and emphysema. Preferably, the subject disease of the composition of the present invention may be COPD. However, the subject disease of the present invention is not limited to those diseases which accompany an applicable irreversible airway obstruction and occur due to pathological changes in the bronchioles and lung parenchyma which are caused by infections in the airway and lung parenchyma.

For the purpose of the present invention, the *Pistacia weinmannifolia* extract, a fraction thereof, or a compound isolated therefrom according to the present invention may be used for the prevention or treatment of COPD.

As used herein, the term "*Pistacia weinmannifolia* extract" refers to all of an extract obtained by extracting the roots, leaves, stems, etc., of *Pistacia weinmannifolia* using a suitable solvent; a diluted or concentrated solution of the extract; a dried product obtained by drying the extract; and a coarse purified product or purified product thereof. The *Pistacia weinmannifolia* extract may be extracted from various organs of natural, hybrid, and modified plants of *Pistacia weinmannifolia*, and in particular, an extract obtained from the stems of *Pistacia weinmannifolia*, etc., but is not limited thereto.

The *Pistacia weinmannifolia* extract of the present invention may be prepared by a conventional extraction method in the art such as sonication extraction, filtration, reflux extraction, etc. *Pistacia weinmannifolia* for use may be purchased from the commercial market or obtained by collecting those grown or cultivated in nature.

The *Pistacia weinmannifolia* extract of the present invention may be isolated according to the conventional method for preparing an extract from a natural product known in the art, i.e., using a conventional solvent under the conventional temperature and pressure conditions.

For the preparation of the *Pistacia weinmannifolia* extract of the present invention, solvents such as water, a $C_1$-$C_4$ alcohol (low-grade anhydrous or hydrous alcohol), or a mixed solvent thereof may be used, but are not limited thereto. For example, the *Pistacia weinmannifolia* extract may be prepared using methanol, and in particular, using 70% to 95% methanol as an extraction solvent. Additionally, for solvent extraction, the extraction may be performed by heat extraction, cold extraction, reflux extraction, or sonication extraction. These extractions may be performed at room temperature or at low temperature or under heat treatment. Subsequently, the *Pistacia weinmannifolia* extract may be obtained by filtration and/or concentration under reduced pressure of the extract, and the extract process may be repeated two or three times, and may include an additional step of filtration, concentration, lyophilization, etc.

In a preferred embodiment of the present invention, the stems of collected *Pistacia weinmannifolia* were dried and pulverized. The pulverized powdered sample was treated with 20 volumes of methanol based on the dry weight of the sample, and a 70% to 95% methanol extract was obtained therefrom. Subsequently, the resultant was subjected to filtration and concentration under reduced pressure and a *Pistacia weinmannifolia* methanol extract was obtained therefrom.

As used herein, the term "fraction" refers to a resultant obtained from a mixture containing various constituting components by a fractionation method to isolate a particular component or group. In the present invention, fraction refers to a resultant obtained from a *Pistacia weinmannifolia* extract by a fractionation method to isolate a particular component or group.

In order to obtain the *Pistacia weinmannifolia* fraction according to the present invention, a conventional solvent for fractionation known in the art, e.g., water; a polar solvent of a low-grade anhydrous or hydrous $C_1$-$C_4$ alcohol such as ethanol and methanol; a non-polar solvent such as hexane, butanol, ethyl acetate, chloroform, and dichloromethane; or a mixed solvent thereof may be used, but the solvent is not limited thereto.

The *Pistacia weinmannifolia* fraction of the present invention may further include those obtained by applying additional purification to the fractionation process. For example, a fraction obtained by passing the *Pistacia weinmannifolia* fraction of the present invention through an ultrafiltration membrane having a predetermined molecular weight cut-off value and a fraction obtained by various purification methods additionally performed by separation via various chromatographies (those prepared for the separation according to size, electric charge, hydrophobicity, or hydrophilicity) are included in the *Pistacia weinmannifolia* fraction of the present invention.

In a preferred embodiment of the present invention, the methanol extract of *Pistacia weinmannifolia* obtained above was suspended by adding distilled water thereto and adding an equal amount of hexane to separate it into a hexane layer and a water layer. After repeating the above process three times, the resultant was filtered and concentrated under reduced pressure to obtain a hexane fraction. Then, the hexane fraction was removed and the remaining water layer was treated with an equal amount of chloroform to obtain a chloroform fraction in the same manner, and the remaining water layer was treated with an equal amount of ethyl acetate to obtain an ethyl acetate fraction in the same manner. The remaining water layer was again treated with an equal amount of butanol to obtain a butanol fraction.

In an exemplary embodiment of the present invention, a methanol extract of *Pistacia weinmannifolia* was loaded and a fraction thereof was obtained at an elution rate of 9 mL/min using a methanol/water [0:100→100:0 (v/v)] solvent. Likewise, active fractions 1 to 7 were obtained.

In an exemplary embodiment of the present invention, cell viability rate was examined by treating cells with six different kinds of active fractions of *Pistacia weinmannifolia* at different concentrations. As a result, no toxicity was observed in cells when treated at a concentration of 1 μM or below (FIG. 5 and Table 3).

Additionally, in an exemplary embodiment of the present invention, cells were treated with six different kinds of active fractions of *Pistacia weinmannifolia* at different concentrations to examine the inhibitory effect against the production of MUC5AC protein, thereby confirming the excellent inhibitory effect of the active fractions compared to the extract (FIG. 7 and Table 4).

Additionally, the *Pistacia weinmannifolia* extract or a fraction thereof may include the compound represented by the following Formula 1 or Formula 2.

[Formula 1]

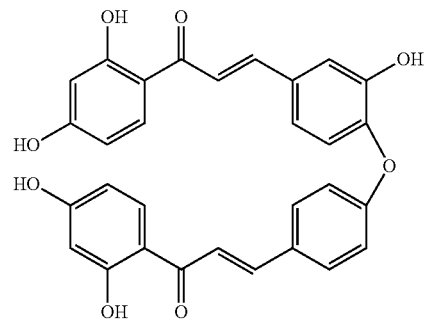

[Formula 2]

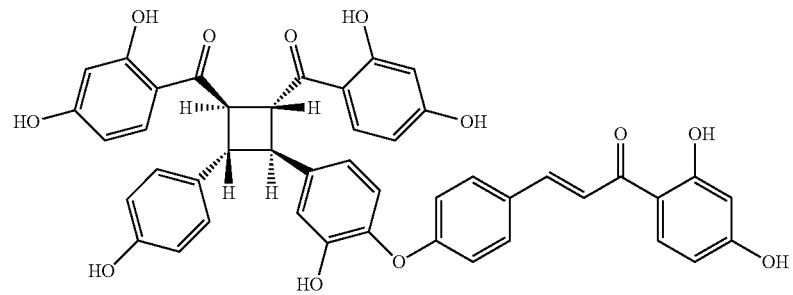

In an exemplary embodiment of the present invention, three kinds of novel active compounds capable of inhibiting inflammatory reactions of COPD were isolated from the *Pistacia weinmannifolia* extract or a fraction thereof. Specifically, the active fraction 5 of the *Pistacia weinmannifolia* extract was eluted again at an elution rate of 14 mL/min using a methanol/water [10:90→100:0 (v/v)] solvent to obtain small fractions. Among the small fractions, a novel compound PW12 represented by Formula 1 and a novel compound PW13 represented by Formula 2 were isolated.

Specifically, regarding the two kinds of novel active compounds, the molecular formula of the compound of Formula 1 (PW12) is $C_{30}H_{22}O_8$ and 2',4'3'',2''',4'''-pentahydroxy-4-O-3''-bichalcone by IUPAC nomenclature, and the present inventors named it as pistachalcone. The molecular formula of the compound of Formula 2 (PW13) is $C_{45}H_{34}O_{12}$ and di-(2,4-dihydroxybenzoyl)-(3,4-dihydroxyphenyl)-(4-hydroxyphenyl)-cyclobutane-3-O-4'-bichalcone by IUPAC nomenclature, and the present inventors named it as pistachalcone B.

In a preferred embodiment of the present invention, cell viability rate was examined by treating cells with the *Pista-* cia weinmannifolia extract or the two different compounds extracted from the fraction of Pistacia weinmannifolia at different concentrations. As a result, no toxicity was observed in cells when treated at a concentration of 1 µM or below (FIG. 6 and Table 3).

Additionally, in an exemplary embodiment of the present invention, cells were treated with the Pistacia weinmannifolia extract or three different compounds extracted from the fraction of Pistacia weinmannifolia at different concentrations to examine their inhibitory effects against the production of MUC5AC protein, thereby confirming their excellent inhibitory effects compared to the extract (FIG. 7 and Table 4).

Cytokines such as TNF-α and CXC chemokines such as MIP-2 are known to be involved in the trafficking activity of neutrophils from pulmonary circulation to pulmonary alveoli. These are cytokines or chemokines which are all associated with inflammation, and in the case of occurrence of COPD, the number of neutrophils increases and the cytokines or chemokines are released. Accordingly, inflammations occur in the airway, muscle walls become thick, and mucus secretion increases, thereby causing an airway obstruction. Once the bronchi become obstructed, the alveoli become dilated and damaged, thereby deteriorating the ability of exchanging between oxygen and carbon dioxide and increasing the risk of respiratory failure. In particular, the expression of these cytokines or chemokines is known to increase in patients with COPD, thus confirming their correlation with the COPD.

Accordingly, COPD responses can be suppressed by inhibiting the secretion of proteins selected from CXCL-1, TNF-α, and MIP-2.

Meanwhile, $CD^{4+}$ cells are known as cells promoting immune functions and the excess increase of the $CD^{4+}$ cells may result in autoimmunity. COPD patients are known to significantly increase the number of $CD^{4+}$ cells compared to that of normal people (Proceedings of the American Thoracic Society, Vol. 4, No. 7 (2007), pp. 512-521).

Meanwhile, in the case of COPD, the number of neutrophils Gr-1$^+$ cells also increases (Eur Respir J 2011; 38: 285-294; Nikota et al. Respiratory Research 2011, 12: 39).

Accordingly, COPD responses can be suppressed by reducing the number of $CD^{4+}$ cells and neutrophils Gr-1$^+$ cells.

In summary, the Pistacia weinmannifolia extract, a fraction thereof, or a compound isolated therefrom of the present invention may have the following activity:

(a) reducing the number of inflammatory cells around the bronchi or the blood vessels and the number of neutrophils;

(b) reducing the number of $CD^{4+}$ cells or neutrophils Gr-1$^+$ cells;

(c) inhibiting the production of CXCL-1;

(d) inhibiting the production of TNF-α; or (e) inhibiting the production of MCP-2.

In an exemplary embodiment of the present invention, the inhibitory effects of the Pistacia weinmannifolia extract and a fraction thereof obtained as described above against COPD were examined. As a result, the methanol extract of the Pistacia weinmannifolia according to the present invention exhibited a significant inhibition in the number of neutrophils in an animal model inhaled with a standard cigarette extract (see Table 5) and also reduced the number of $CD^{4+}$ cells and neutrophils Gr-1$^+$ cells (see Table 6), CXCL-1 (see Table 7), TNF-α (see Table 8), and MIP-2 (see Table 9).

From the results above, it was confirmed that the Pistacia weinmannifolia extract and a fraction thereof of the present invention can be effectively used for the prevention and treatment of COPD.

Accordingly, the present invention provides a composition for preventing or treating COPD, containing the Pistacia weinmannifolia extract, a fraction thereof, or a compound isolated therefrom as an active ingredient, and a pharmaceutically acceptable carrier.

The COPD may be selected from the group consisting of chronic obstructive bronchitis, chronic bronchiolitis, emphysema, multiple sclerosis, and acute and chronic inflammation, and preferably a chronic obstructive disease, but the applicable multiple sclerosis, and acute and chronic lung diseases are not limited by the same.

As used herein, the term "chronic obstructive pulmonary disease (COPD)" is a respiratory disease, in which an abnormal inflammatory reaction occurs in the lung by the inhalation of harmful particles or gas(es) and a progressive airway limitation occurs, thereby deteriorating pulmonary functions and inducing respiratory distress. Major symptoms of COPD include difficulty breathing, etc., along with chronic cough or chronic phlegm (sputum), and the representative therapeutic agents may include bronchodilators such as beta agonists, anticholinergics, methylxanthines, etc., and inhaled corticosteroids, etc. In the present invention, COPD may refer to chronic bronchitis or emphysema, but is not limited thereto.

As used herein, the term "chronic bronchitis" refers to a disease in which sputum production lasts for two consecutive years with at least three months of sputum production each year and a long-lasting cough is accompanied. Smoking, air pollution, and bronchial damage by stimulus due to occupational exposure appear to be the possible causes of the disease, and major symptoms include chronic cough, sputum production, difficulty breathing during exercises, etc. Additionally, an acute deterioration, which is a characteristic of COPD, may occur, during which difficulty breathing rapidly worsens within a few hours to a few days, the amount of sputum may increase or the features of the sputum may change from being mucous to being pyogenic while its color turns to dark yellow or bluish and its viscosity increases thus making it difficult to spit out the sputum.

As used herein, the term "emphysema" refers to an abnormal and permanent dilated state of peripheral airway and alveoli caused by the destruction of the distal airspace of terminal bronchioles. Emphysema occurs by the inhalation of harmful particles and gases and the most meaningful clinical risk factor is known to be smoking. Major symptoms of emphysema include chronic cough, sputum, difficulty breathing, etc.

As used herein, the term "prevention" refers to" to all activities capable of inhibiting or delaying the occurrence of multiple sclerosis, and acute and chronic lung diseases including COPD by administering a composition containing according to the present invention.

As used herein, the term "treatment" refers to" all activities capable of alleviating or improving the symptoms of multiple sclerosis, and acute and chronic lung diseases including COPD by administering a composition containing according to the present invention.

The pharmaceutical composition of the present invention may be used as a single formulation or a complex formulation by further including a drug(s), which is(are) known to have approved effects for the treatment of multiple sclerosis, and acute and chronic lung diseases.

As used herein, the term "pharmaceutically acceptable" refers to the properties of neither significantly stimulating a bioorganism nor inhibiting the biological activities and characteristics of the active material(s) for administration. The pharmaceutical composition of the present invention including a pharmaceutically acceptable carrier may be prepared in various types of oral or parenteral formulations. For the preparation of formulations, commonly used fillers, extenders, binders, humectants, disintegrating agents, diluents such as surfactants or excipients may be used.

Solid formulations for oral administration may include tablets, pills, powders, granules, capsules, etc. The solid formulations may be prepared by adding at least one excipient, e.g., starch, calcium carbonate, sucrose or lactose, gelatin, etc. Additionally, lubricants such as magnesium stearate, talc, etc., may be used in addition to the simple excipients. Examples of liquid formulations for oral administration may include suspensions, formulations for internal use, emulsions, syrups, etc., and various kinds of excipients, e.g., humectants, sweeteners, fragrances, preservatives, etc., may be used in addition to simple diluents such as water and liquid paraffin. Formulations for parenteral administration may include sterile aqueous solutions, non-aqueous solvents, suspensions, emulsions, lyophilized preparations, and suppositories. For non-aqueous solvents and suspensions, propylene glycol, polyethylene glycol, a vegetable oil such as olive oil, an injectable ester such as ethyloleate may be used. Examples of bases for suppositories may include Witepsol, macrogol, Tween 61, cacao butter, laurinum, glycerogelatin, etc.

The pharmaceutical composition of the present invention may have any formulation type selected from the group consisting of tablets, pills, powders, granules, capsules, suspensions, formulations for internal use, emulsions, syrups, sterile aqueous solutions, non-aqueous solvents, suspensions, emulsions, lyophilized preparations, and suppositories.

Additionally, the pharmaceutical composition of the present invention may contain a pharmaceutically effective amount of the *Pistacia weinmannifolia* extract, a fraction thereof, or a compound isolated therefrom. As used herein, the term "pharmaceutically effective amount" refers to an amount sufficient to treat diseases, at a reasonable benefit/risk ratio applicable to any medical treatment, and the level of the effective dose may be determined according to factors including the type of a subject and severity, age, sex, activity of drug(s), sensitivity to drug(s), administration time, administration route and excretion rate, duration of treatment, and drug(s) for concurrent administration, and other factors well known in the medical arts. The pharmaceutical composition of the present invention may be administered alone or in combination with other therapeutic agent(s) and it may be administered sequentially or simultaneously with conventional therapeutic agents. The composition may be administered in a single or multiple dosage form. It is important to administer the composition in the minimum amount that may exhibit the maximum effect without causing side-effects, in view of all of the above-described factors, and this amount can be easily determined by a person skilled in the art. The pharmaceutical composition of the present invention may be preferably contained to the *Pistacia weinmannifolia* extract, a fraction thereof, or a compound isolated therefrom, in an amount of 0.001 µg/mL to 1500 µg/mL, and more preferably 0.001 µg/mL to 1,000 µg/mL. Alternatively, the composition of the present invention may contain the *Pistacia weinmannifolia* extract or a fraction thereof in an amount of 1 wt % to 10 wt %, and in particular, 5 wt % to 10 wt %. Additionally, the composition of the present invention may contain the compounds isolated from *Pistacia weinmannifolia* in the present invention, e.g., compounds represented by Formula 1 and Formula 2 in an amount of 0.01 wt % to 10 wt %.

In another aspect, the present invention provides a method for preventing or treating COPD by administering a pharmaceutical composition containing a *Pistacia weinmannifolia* extract, a fraction thereof, or a compound isolated therefrom to a subject in need of the prevention or treatment of COPD.

The *Pistacia weinmannifolia* extract, a fraction thereof, and a compound isolated therefrom are the same as explained above.

The COPD may be selected from the group consisting of chronic obstructive bronchitis, chronic bronchiolitis, emphysema, multiple sclerosis, and acute and chronic inflammation, and preferably COPD, but the chronic obstructive bronchitis, chronic bronchiolitis, emphysema, multiple sclerosis, and acute and chronic inflammatory diseases to which the present invention can be applicable are not limited thereto.

In the present invention, the subject refers to all animals including humans in which a chronic obstructive pulmonary disease has occurred or can occur, and the subject can be effectively treated by administering a pharmaceutical composition containing the compound of the present invention or a pharmaceutically acceptable salt thereof to the subject suspected of having the chronic obstructive pulmonary disease. Specifically, the subject is one which requires prevention or treatment of COPD and chronic obstructive bronchitis, chronic bronchiolitis, emphysema, multiple sclerosis, and acute and pulmonary diseases, etc., and the subject may include not only humans but also mammals such as cattle, horses, sheep, pigs, goats, camels, antelopes, dogs, cats, etc., which require treatment of similar symptoms thereof, but is not limited thereto.

As used herein, the term "administration" refers to introduction of the pharmaceutical composition of the present invention into a patient using any suitable method. The composition of the present invention may be orally or parenterally administered via various routes, as long as it can reach the target tissue.

The method of treating COPD and chronic obstructive bronchitis, chronic bronchiolitis, emphysema, multiple sclerosis, and acute and pulmonary diseases includes administering a *Pistacia weinmannifolia* extract, a fraction thereof, or a compound isolated therefrom in a pharmaceutically effective amount. That is, the method of treating COPD and chronic obstructive bronchitis, chronic bronchiolitis, emphysema, multiple sclerosis, and acute and pulmonary diseases includes administering a pharmaceutical composition of the present invention containing the *Pistacia weinmannifolia* extract, a fraction thereof, or a compound isolated therefrom in a pharmaceutically effective amount.

As used herein, the term "pharmaceutically effective amount" refers to an amount sufficient for the treatment of diseases at a reasonable benefit/risk ratio applicable to a medical treatment, and the level of the effective dose may be determined based on the factors including the kind of a subject, severity of illness, age, sex, type of disease, drug activity, drug sensitivity, administration time, administration route and excretion rate, duration of treatment, factors including drug(s) to be concurrently used in combination, and other factors well known in the medical field. The composition of the present invention may be administered as an individual therapeutic agent, in combination with other therapeutic agents, or sequentially or simultaneously with a conventional therapeutic agent(s), and may be administered once or multiple times. It is important to administer an amount to obtain the maximum effect with a minimum amount without adverse effects considering the factors described above, and these factors can easily be determined by one of ordinary skill in the art. A preferable dose of the composition of the present invention may vary depending on the health conditions and body weight of a patient, severity of illness, drug type, administration route, and duration. A suitable daily total dose may be determined by a doctor within the correct medical determination, and in general, the pharmaceutical composition of the present invention may be administered in an amount of 0.001 mg/kg to 1000 mg/kg, preferably 0.05 mg/kg to 200 mg/kg, and more preferably 0.1 mg/kg to 100 mg/kg singly or divided into several times per day. The subject to apply the composition is not particularly limited but any subject which requires the prevention or treatment of chronic obstructive pulmonary diseases can be applicable. For example, the composition can be applicable to any subject including non-human animals such as monkeys, dogs, cats, rabbits, guinea pigs, rats, mice, cattle, sheep, pigs, goats, etc., humans, birds, and fish, and the administration method includes, without limitation, any conventional method in the art. For example, the composition may be administered orally or by rectal-, intravenous-, intramuscular-, intrauterine epidural-, or intraventricular injection.

In still another aspect, the present invention provides a use of a *Pistacia weinmannifolia* extract, a fraction thereof, or a compound isolated therefrom for the prevention or treatment of chronic obstructive pulmonary diseases.

In still another aspect, the present invention provides a food composition for preventing or improving chronic obstructive pulmonary diseases containing a *Pistacia weinmannifolia* extract, a fraction thereof, or a compound isolated therefrom.

The food composition of the present invention may further contain a sitologically acceptable carrier.

The *Pistacia weinmannifolia* extract, a fraction thereof, or a compound isolated therefrom and chronic obstructive pulmonary diseases are the same as explained above.

The food composition may have the function of aiding the inhibition of COPD and chronic obstructive bronchitis, chronic bronchiolitis, emphysema, multiple sclerosis, and acute and pulmonary diseases.

The food composition of the present invention may be formulated into pills, powders, granules, tablets, capsules, or liquids. The type of foods, to which the *Pistacia weinmannifolia* extract, a fraction thereof, or a compound isolated therefrom can be contained, may not be particularly limited, and they may include various kinds of beverages, gums, teas, vitamin complexes, health supplementary foods, etc.

The food composition may further contain other components, which do not interfere with the inhibitory effect against chronic obstructive bronchitis, chronic bronchiolitis, emphysema, multiple sclerosis, and acute and pulmonary diseases, in addition to the *Pistacia weinmannifolia* extract, a fraction thereof, or a compound isolated therefrom, and the kinds of other components to be further added are not particularly limited. For example, various kinds of herbal drug extracts, sitologically acceptable food supplement additives, natural carbohydrates, etc., may be contained as additional components, as is the case with conventional foods.

As used herein, the term "food supplement additive" refers to a constituting element that can be added into foods, and anything that can be added in the preparation of various types of health functional foods may be appropriately selected for use by one of ordinary skill in the art. Examples of the food supplement additives various nutrients, vitamins, minerals (electrolytes), synthetic and/or natural flavoring agents, colorants and fillers, pectic acid or salts thereof, alginic acid or salts thereof, organic acids, protective colloidal thickening agents, pH adjusters, stabilizers, preservatives, glycerin, alcohols, carbonating agents used in carbonated beverages, etc., but the kind of the food supplement additives is not limited to these examples.

Examples of the natural carbohydrates may include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. Additionally, natural flavoring agents (e.g., thaumatin, stevia extract (e.g., rebaudioside A, glycyrrhizin)) and synthetic flavoring agents (e.g., saccharin, aspartame, etc.) may be advantageously used as flavoring agents.

The food composition of the present invention may contain health functional foods. As used herein, the term "health functional food" refers to a food prepared/processed in the form of a tablet, a capsule, powder, granule, a liquid, a pill, etc., using a raw material or component having a useful function for the human bodies. As used herein, the term "functional" refers to being able to achieve useful effects for health use such as controlling nutrients regarding the structures and functions of human bodies or physiological actions. The health functional food of the present invention can be prepared by a conventional method used in the art, and raw material(s) and component(s) conventionally added in the art may be added during the preparation. Additionally, unlike other common drugs, the health functional food may be prepared using foods as raw materials, and thus it has the advantage of avoiding side-effects associated with long-term drug administration and it may be very portable.

When the composition of the present invention is used by adding into a health functional food, the composition itself may be added or may be used along with other health functional food or health functional food component(s), and appropriately used according to the conventional method. The amount of active ingredient(s) to be combined may be appropriately determined according to the purposes of use (prevention, health, or therapeutic treatment). Generally, in the preparation of foods, the *Pistacia weinmannifolia* extract or a fraction thereof may be added in an amount of 1 wt % to 10 wt %, preferably 5 wt % to 10 wt % based on the composition of raw materials. However, in a case of a long-term administration for the purpose of health, hygiene, or health control, the amount less than the above dose may also be used.

The kinds of foods of the present invention are not particularly limited. Examples of the foods in which pinosylvin or a pharmaceutically acceptable salt thereof may be added may include meats, sausages, breads, chocolates, candies, snacks, cookies, pizzas, ramen, other noodles, gums, dairy products including ice cream, various kinds of soups, beverages, teas, drinks, alcoholic beverages, vitamin complexes, etc., and may include all kinds of health functional foods from the conventional point of view.

As used herein, the term "improvement" refers to all of the activities that can improve or advantageously change the symptoms of the subject suspected of having or diagnosed with a chronic obstructive pulmonary disease by administering the above composition.

The kinds of health functional foods that can contain the composition of the present invention are not particularly limited. Examples of the health functional foods may include meats, sausages, breads, chocolates, candies, snacks, cookies, pizzas, ramen, other noodles, gums, dairy products including ice cream, various kinds of soups, beverages, teas, drinks, alcoholic beverages, vitamin complexes, etc., and may include all kinds of health functional foods from the conventional point of view, and may also include foods used as animal feeds.

Additionally, in a case when the health functional food composition of the present invention is used in the form of a beverage, various sweetening agents, flavoring agents, or natural carbohydrates may be contained as additional components, as is the case of conventional beverages. Examples of the natural carbohydrates may include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. The natural carbohydrates are preferably contained in an amount of about 0.01 g to about 0.04 g per 100 mL of the composition of the present invention, and more preferably, 0.02 g to about 0.03 g, but the amount is not limited to the above range. Additionally, the sweetening agents may be natural sweetening agents (e.g., thaumatin, stevia extract, etc.) and synthetic sweetening agents (e.g., saccharin, aspartame, etc.).

Additionally, the health functional food composition of the present invention may further contain various nutrients, vitamins, electrolytes, flavoring agents, colorants, pectic acid or salts thereof, alginic acid or salts thereof, organic acids, protective colloidal thickening agents, pH adjusters, stabilizers, preservatives, glycerin, alcohols, carbonating agents used in carbonated beverages, etc. Additionally, the health functional food composition of the present invention may contain fruit flesh for preparing natural fruit juices, fruit juices, and vegetable juices.

In still another aspect, the present invention provides compounds isolated from *Pistacia weinmannifolia*, an extract or fraction thereof, represented by Formula 1 or Formula 2.

In an exemplary embodiment of the present invention, two novel active compounds capable of inhibiting COPD were isolated from a *Pistacia weinmannifolia* extract or a fraction thereof. Specifically, the active fraction 5 of *Pistacia weinmannifolia* extract was eluted again at an elution rate of 14 mL/min using a methanol/water [10:90→100:0 (v/v)] solvent to obtain small fractions. Among the small fractions, a novel compound PW12 represented by Formula 1 and a novel compound PW13 represented by Formula 2 were isolated. The present inventors named the novel compound PW12 represented by Formula 1 as pistachalcone and novel compound PW13 represented by Formula 2 as pistachalcone B.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1. Preparation of a *Pistacia weinmannifolia* Extract, Fraction, and Compound Thereof 1-1. Preparation of a *Pistacia weinmannifolia* Extract A methanol extract of *Pistacia weinmannifolia* J. Poiss. Ex Franch was purchased from the Overseas Plant Extract Bank of the Overseas Biomaterial Hub Center of the Korean Research Institute of Bioscience and Biotechnology (KRIBB).

Regarding the extraction process, *Pistacia weinmannifolia* stems (20 kg) were collected and the water contained therein was removed by a dryer (50° C. to 55° C.) under natural drying (drying in the shade) and ground. The ground powdered sample was treated with methanol (30 L) based on the dry weight of the ground powdered sample and was

[Formula 1]

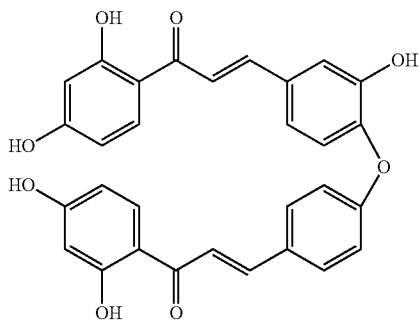

[Formula 2]

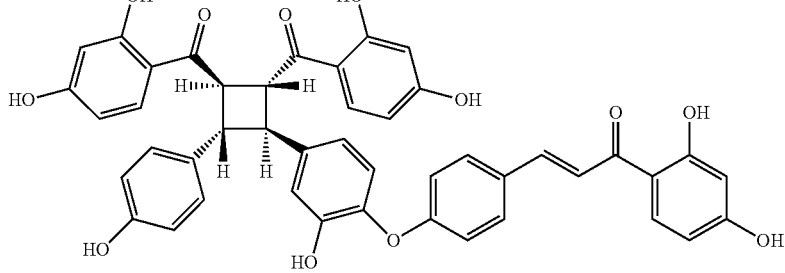

subjected to extraction at room temperature. Then, the resultant was filtered and concentrated under reduced pressure to obtain a *Pistacia weinmannifolia* methanol extract (542.2 g). The *Pistacia weinmannifolia* methanol extract obtained subsequently in the following experiment was named as a total extract.

1-2. Preparation of a Fraction of *Pistacia weinmannifolia*

The total *Pistacia weinmannifolia* extract (542.2 g) obtained in Example 1-1 was suspended by adding water (5 L) and treated with an equal amount of hexane to separate the mixture into a water layer and a hexane layer. The entire process was repeated three times in the same manner, and the resultants were filtered and concentrated under reduced pressure to separate a hexane fraction (48.5 g). After separating the hexane layer in the same manner, the remaining water layer was separated in the same manner by adding an equal amount of chloroform to obtain a chloroform fraction (16.3 g). In the same manner, the chloroform layer was separated and the remaining water layer was separated in the same manner by adding an equal amount of ethyl acetate to obtain an ethyl acetate fraction (53.7 g). In the same manner, the ethyl acetate was separated and the remaining water layer was separated in the same manner by adding an equal amount of butanol to obtain a butanol fraction (114 g). The remaining water layer was concentrated to obtain a water fraction (186.5 g).

1-3. Preparation of an Active Fraction of *Pistacia weinmannifolia*

For MPLC analysis, a column (20 mm×250 mm; Resin; Zeoprep C18, 10 μm) was installed to an MPLC device (Interchim) and methanol extract (2 g) was loaded repeatedly. In particular, a methanol/water [0:100→100:0 (v/v)] solvent was used at an elution rate of 9 mL/min and active fractions (Fr. 1 to Fr. 7) were obtained by detecting at a wavelength of UV 200 nm to 400 nm. The MPLC analysis results are shown in FIG. 1 and Table 1.

1-4. Analysis of an Extract and a Fraction of *Pistacia weinmannifolia*

To examine the active fractions of the ethyl acetate fraction of *Pistacia weinmannifolia* obtained in Example 1-2, the fractions were analyzed by ultra performance liquid chromatography (UPLC).

First, for the UPLC analysis, the ethyl acetate fraction (53.7 g) was filtered once with a 0.25 mm membrane filter for UPLC. After installing a column (Waters BEH C18 column, 2.1×100 mm, 1.7 mm) to the UPLC device (Waters UPLC-Q-TOF), each of the filtered fractions was loaded in an amount of 0.3 μL.

In particular, the solvent used for the UPLC analysis was acetonitrile+0.1% formic acid/water+0.1% formic acid [10:90→100:0 (v/v)], and the elution rate was set at 0.4 mL/minute. With respect to the active fractions and separated materials, the degree of separation was confirmed from the UPLC in the form of chromatography at a wavelength of UV 200 nm to 400 nm via mass spectrometry (MS) using a detector.

The results of the UPLC-PDA-QTOF-MS analysis are shown in FIG. 2 and FIGS. 3A and 3B.

1-5. Extraction of a Compound Derived from *Pistacia weinmannifolia*

Novel compounds were isolated from the fraction Fr. 5 obtained in Example 1-3 by a method described below.

Specifically, after installing a column (YMC-DispoPack AT, 40×500 mm, 45 μm) to the MPLC device (YMC Lc-Forte/R), the active fraction Fr. 5 (821 mg) was loaded. In particular, methanol/water [10:90→100:0 (v/v)] was used as a solvent, and the elution rate was set at 14 mL/minute, and detections were performed at wavelengths of UV 254-, 280-, and 320 nm and thereby subfractions (Fr. 5A-5G) were obtained.

With respect to the subfraction Fr. 5E (297 mg), a column (YMC-Pack ODS AQ-HG, 250×20 mm, 5 μm) was installed to the Prep-HPLC device (Gilson) and the active fraction was loaded in an amount of 10 mg/mL. In particular, acetonitrile/water [10:90→100:0 (v/v)] was used as a solvent, and the elution rate was set at 14 mL/minute, and detections were performed at wavelengths of UV 254 nm and 280 nm and thereby a compound, PW12 (15.3 mg), which has a novel structure and physical properties represented by Formula 1, was obtained (Table 2 and FIG. 4B).

With respect to the subfraction Fr. 5F (156 mg), a column (YMC-Pack ODS AQ-HG, 250×20 mm, 5 μm) was installed to the Prep-HPLC device (Gilson) and the active fraction was loaded in an amount of 10 mg/mL. In particular, acetonitrile/water [10:90→100:0 (v/v)] was used as a solvent, and the elution rate was set at 14 mL/minute, and detections were performed at wavelengths of UV 254 nm and 280 nm and thereby a compound, PW13 (20.5 mg), which has a novel structure and physical properties represented by Formula 1, was obtained (Table 2 and FIG. 4B).

TABLE 1

| | Fraction | Solvent Condition | Number (Bottle No.) | Weight (mg) |
|---|---|---|---|---|
| Fr. 1 | Fraction 1 | 0-26 | 1-12 | 32.1 |
| Fr. 2 | Fraction 2 | 26-40 | 13-18 | 253.7 |
| Fr. 3 | Fraction 3 | 40-53 | 19-24 | 400.2 |
| Fr. 4 | Fraction 4 | 53-65 | 25-29 | 85.9 |
| Fr. 5 | Fraction 5 | 65-100 | 30-45 | 65.3 |
| Fr. 6 | Fraction 6 | 100 | 46-60 | 27.5 |

TABLE 2

Results of UPLC-PDA-QTOF-MS analysis of novel compounds

| Category | Data |
|---|---|
| PW12 (Formula 1) | Amorphous powder; HRESIMS m/z 509.1236 [M − H]−; $^1$H-NMR (400 MHz, MeOD) δ 7.73 (1H, d, J = 8.8 Hz, H-2), 6.98 (1H, d, J = 8.8 Hz, H-3), 6.98 (1H, d, J = 8.8 Hz, H-5), 7.73 (1H, d, J = 8.8 Hz, H-6), 6.28 (1H, d, J = 2.3 Hz, H-3'), 6.40 (1H, dd, J = 8.8, 2.3 Hz, H-5'), 7.94 (1H, d, J = 8.8 Hz, H-6'), 7.64 (1H, d, J = 15.3 Hz, H-α), 7.80 (1H, d, J = 15.3 Hz, H-β), 7.50 (1H, d, J = 2.0 Hz, H-2''), 7.04 (1H, d, J = 8.4 Hz, H-5''), 7.53 (1H, d, J = 8.4, 2.0 Hz, H-6''), 6.28 (1H, d, J = 2.3 Hz, H-3'''), 6.40 (1H, dd, J = 8.8, 2.3 Hz, H-5'''), 7.94 (1H, d, J = 8.8 Hz, H-6'''), 7.64 (1H, d, J = 15.3 Hz, H-α'), 7.80 (1H, d, J = 15.3 Hz, H-β'); $^{13}$C-NMR (100 MHz, MeOD) δ. 130.6, 131.6, 117.8, 161.8, 117.8, 131.6, 114.7, 167.6, 103.8, 166.5, 109.2, 193.3, 133.5, 120.2, 144.6, 129.0, 123.4, 144.2, 153.5, 118.8, 128.6, 114.7, 167.5, 103.8, 166.4, 109.2, 133.5, 119.7, 144.7, 193.4 |
| PW13 (Formula 2) | Amorphous powder; HRESIMS m/z 765.1972 [M − H]−. $^1$H-NMR (400 MHz, MeOD) δ 6.86 (1H, d, J = 2.0 Hz, H-2), 6.98 (1H, d, J = 8.4 Hz, H-5), 7.15 (1H, dd, J = 8.4, 2.0 Hz, H-6), 3.64 (1H, dd, J = 9.2, 8.8 Hz, H-7), 4.45 (1H, dd, J = 8.8, 7.8 Hz, H-8), 6.19 (1H, d, J = 2.3 Hz, H-12), 6.06 (1H, dd, J = 8.8, 2.3 Hz, H-14), 7.31 (1H, d, J = 8.8 Hz, H-15), 7.64 (2H, d, J = 8.4 Hz, H-2', 6'), 6.85 (2H, d, J = 8.4 Hz, H-3', 5'), 6.28 (1H, d, J = 2.3 Hz, H-9'), 6.41 (1H, dd, J = 8.8, 2.3 Hz, H-11'), 7.98 (1H, d, J = 8.8 Hz, H-12'), 7.66 (1H, d, J = 15.4 Hz, H-α), 7.79 (1H, d, J = 15.4 Hz, H-β), 7.12 |

TABLE 2-continued

Results of UPLC-PDA-QTOF-MS analysis of novel compounds

| Category | Data |
|---|---|
| | (2H, d, J = 8.4 Hz, H-2", 6"), 6.74 (2H, d, J = 8.4 Hz, H-3", 5"), 3.71 (1H, dd, J = 9.2, 8.8 Hz, H-7"), 4.45 (1H, dd, J = 8.8, 7.8 Hz, H-8"), 6.23 (1H, d, J = 2.3 Hz, H-12"), 6.15 (1H, dd, J = 8.8, 2.3 Hz, H-14"), 7.31 (1H, d, J = 8.8 Hz, H-15"); $^{13}$C-NMR (100 MHz, MeOD) δ 134.7, 122.4, 143.8, 149.7, 118.8, 125.6, 150.2, 47.7, 203.2, 113.1, 167.0, 109.1, 167.0, 103.7, 134.3, 130.5, 131.4, 117.9, 161.7, 114.6, 167.4, 109.5, 167.6, 103.9, 133.5, 120.2, 144.7, 193.3, 133.2, 129.6, 116.5, 157.8, 49.6, 47.7, 202.9, 113.1, 167.0, 109.3, 167.0, 103.8, 134.3. |

Example 2. Cytotoxicity Test

To confirm the cytotoxicity of a *Pistacia weinmannifolia* extract, a fraction thereof, and a compound isolated therefrom, which were prepared and extracted in Example 1, experiments were performed by applying the method described in the existing references (Ishiyama et al., Talanta, 44, pp. 1299-1305, 1997; Tominaga et al., *Anal. Commun.*, 36, pp. 47-50, 1999).

2-1. Preparation of Cells and Cultivation

H292 (CRL-1848) was purchased from the American Type Culture Collection (ATCC). The H292 cells were cultured in RPMI medium (SH30027.01, RPMI 1640, Gibco) containing 10% fetal bovine serum and antibiotics, and cultured in the condition of humidified 5% $CO_2$ atmosphere at 37° C. TNF-α was purchase from a company (300-01A, Peprotech, USA) and used.

2-2. Cell Viability Assay

The cells in a medium (GM) were placed in a 96-well plate at a density of (1×10$^3$ cells/well). After 24 hours, the cells were cultured along with a sample for one day. The cell viability rate was read via trivalues according to the manufacturer's manual using the Cell Counting Kit-8 (CK04-01, Dojindo Molecular Technologies, ML). The absorbance was measured using the VERSAmax microplate reader (SMP500-14915, Molecular Devices, USA) and the measured absorbance was converted into a cell number via a standard curve.

2-3. Evaluation of Cytotoxicity of a *Pistacia weinmannifolia* Extract, a Fraction, and a Compound Isolated Therefrom H292 cells, human mucosa cells of lung cancer, were suspended in RPMI medium (Gibco) containing 10% fetal bovine serum in a concentration of 5×10$^4$ cells/mL, inoculated to a 96 well-plate in an amount of 100 μL per each well, and allowed to be attached thereto for 12 hours. Six active fractions of *Pistacia* and 3 single compounds (PW11, PW12, and PW13) were treated according to concentrations, and cultured for 24 hours. As explained in the cell counting CCK-8 kit (Dojindo Molecular Technologies, ML), the CCK-8 solution (10 μL) was mixed with the medium (90 μL). The mixture (100 μL) was added to each well, reacted for the minimum 30 minutes to the maximum 4 hours, and the absorbance was measured at 570 nm. The cell viability was calculated according to Equation 1 above with reference to the negative control, which was treated with DMSO in a concentration of 0.2%, set at 100%. The results are shown in Table 3 below.

Cell Viability (%)=[value at $OD$ 570 nm after treatment with an extract/value at $OD$ 570 nm (negative control)]×100  [Equation 1]

TABLE 3

| Sample | Concentration | H292 Cell Viability Rate (%, Mean ± SD) |
|---|---|---|
| Negative Control | 0 | 99.99 ± 3.79 |
| *Pistacia weinmannifolia* Extract (μg/mL) | 0.125 | 96.46 ± 1.50 |
| | 0.25 | 91.61 ± 6.12 |
| | 0.5 | 103.14 ± 1.47 |
| | 1 | 103.68 ± 2.89 |
| | 2.5 | 106.45 ± 1.60 |
| | 5 | 103.84 ± 1.42 |
| *Pistacia weinmannifolia* Fraction 6 (μg/mL) | 0.125 | 92.61 ± 1.39 |
| | 0.25 | 96.30 ± 3.57 |
| | 0.5 | 99.68 ± 2.31 |
| | 1 | 107.06 ± 6.47 |
| | 2.5 | 81.93 ± 2.31 |
| | 5 | 52.72 ± 0.48 |
| Compound PW11 (μM) | 0.125 | 97.60 ± 1.83 |
| | 0.25 | 98.05 ± 0.93 |
| | 0.5 | 104.65 ± 0.79 |
| | 1 | 90.24 ± 4.34 |
| Compound PW12 (μM) | 0.125 | 95.80 ± 2.90 |
| | 0.25 | 96.47 ± 3.21 |
| | 0.5 | 104.50 ± 1.32 |
| | 1 | 115.88 ± 0.50 |
| Compound PW13 (μM) | 0.125 | 104.80 ± 2.34 |
| | 0.25 | 103.53 ± 3.07 |
| | 0.5 | 126.28 ± 7.75 |
| | 1 | 71.92 ± 5.47 |

As a result of the experiment performed to examine the cell viability of H292 cells according to the concentration of the *Pistacia weinmannifolia* extract, a fraction thereof, and a compound isolated therefrom, it was confirmed that there is no cytotoxicity in a concentration below 1 μM, as shown in Table 3 above.

Example 3. Effect of Inhibiting the Production of MUC5AC Protein

To analyze the effects of the *Pistacia weinmannifolia* extract, a fraction thereof, and a compound isolated therefrom, prepared and extracted in Example 1, on the prevention and treatment of inflammatory diseases such as COPD, the inhibitory effect of the *Pistacia weinmannifolia* extract, a fraction thereof, and a compound isolated therefrom against the secretion of a related protein, MUC5AC. In this regard, to confirm the inhibitory effect of the samples in Examples on the production of MUC5AC protein, experiments were performed using the method described in the reference (Sikder, M A. et al., *Phytotherapy research*: PTR. 28, 62-8, 2014).

3-1. Effect of Inhibiting the Production of MUC5AC Protein by a *Pistacia weinmannifolia* Extract, a Fraction, and a Compound Isolated Therefrom The supernatant, which was recovered for the immunoassay of the produced MUC5AC, was aliquoted into a 96 well-plate in an amount of 50 μL and dried in a homeostat set at 50° C. The resultant was washed with PBS containing 1% BSA, reacted with MUC5AC antibody (ab3649, abcam) at room temperature for one hour, and aliquoted with the secondary antibody and reacted for one hour. The resultant was rewashed, reacted with 3,3',5,5'-tetramethylbenzidine peroxide solution (54827-17-7, Sigma-Aldrich) for 20 minutes, and the reaction was stopped with a sulfuric acid solution and the coloration was measured at 450 nm using a microplate reader (VERSAmax microplate reader, SMP500-

14915, Molecular Devices, USA). The results are represented by the graph in FIG. 1 and are also shown in Table 4 below.

TABLE 4

Inhibitory effects of a *Pistacia weinmannifolia* extract, a fraction thereof, and a compound isolated therefrom against the production of MUC5AC induced by TNF-α

| Sample | Conc. (µM) | TNF-α (20 ng/mL) | Amount of MUC5AC Secretion (Relative % to TNF-α Treated Group) | Inhibition Rate (%) |
|---|---|---|---|---|
| Negative Control | 0 | − | 42.58 ± 1.38 | 57.42 |
| TNF-α Treated Group | 0 | + | 100.00 ± 3.24 | 0 |
| *Pistacia weinmannifolia* Extract | 5 | + | 79.93 ± 4.79 | 20.07 |
| | 2.5 | + | 87.35 ± 8.13 | 12.65 |
| | 1 | + | 92.82 ± 3.90 | 7.18 |
| | 0.5 | + | 92.34 ± 10.81 | 7.66 |
| | 0.25 | + | 103.16 ± 4.96 | 0 |
| | 0.125 | + | 115.21 ± 5.93 | 0 |
| *Pistacia weinmannifolia* Fraction 6 | 5 | + | 56.20 ± 3.24 | 43.80 |
| | 2.5 | + | 69.95 ± 2.35 | 30.05 |
| | 1 | + | 71.29 ± 3.80 | 28.71 |
| | 0.5 | + | 76.76 ± 3.75 | 23.24 |
| | 0.25 | + | 93.43 ± 7.90 | 6.57 |
| | 0.125 | + | 102.07 ± 7.66 | 0 |
| Compound PW11 | 1 | + | 76.95 ± 8.13 | 23.05 |
| | 0.5 | + | 79.67 +1.14 | 20.33 |
| | 0.25 | + | 86.64 ± 3.99 | 13.36 |
| | 0.125 | + | 88.18 ± 9.42 | 11.82 |
| Compound PW12 | 1 | + | 69.74 ± 8.56 | 30.26 |
| | 0.5 | + | 69.50 ± 5.37 | 30.50 |
| | 0.25 | + | 74.23 ± 12.98 | 25.77 |
| | 0.125 | + | 75.77 ± 7.66 | 24.23 |
| Compound PW13 | 1 | + | 73.76 ± 2.68 | 26.24 |
| | 0.5 | + | 77.30 ± 2.33 | 22.70 |
| | 0.25 | + | 82.39 ± 3.10 | 17.61 |
| | 0.125 | + | 83.92 ± 9.77 | 16.08 |

Example 4. Evaluation of the Effect of a Animal Model with COPD Induced by a Standard Cigarette Extract 4-1. Experimental Animals and Induction of Bronchial Chronic Obstructive Pulmonary Disease In this experiment, 8-week-old male BALB/c mice with an average body weight of about 20 g were used as experimental animals. After an adaptation period for a week, the animals, in which no abnormalities were observed in basic physical examination, were subjected to the experiment.

Sixty cigarettes of a standard cigarette, Coresta Monitoring Cigarette 7 (CM7; Heinr Borgwaldt, Germany), isopropanol, ethanol (Merck, Germany), and n-heptadecane (Sigma-Aldrich, USA) were used. As an experimental equipment, an automatic smoking machine (ISO 3308 standard, an automatic smoking device, Model: RM20, Heinr Borgwaldt) was used.

Specifically, the collection of standard cigarette CM7 smoke condensates was performed in a smoking room (temperature: 22±2° C.; relative humidity: 60±5%) according to the ISO 3402 standard, and the cigarettes were smoked using an RM20 (Heinr Borgwaldt, Germany) automatic smoking machine (ISO 3308 standard) according to the ISO 3308 standard under the following conditions: smoke volume: 35.0±0.3 mL; smoking cycle: 60±0.5 seconds; smoking time: 2.00±0.02 seconds; and tip paper length+3 mm (overwrap+3 mm). Additionally, cigarette smoke condensates were collected on a 92 mm Cambridge filter, ISO 3308 standard) (ISO 3308, 2000).

The Cambridge filter having the cigarette smoke condensates collected thereon was separated from a cigarette holder and placed in each of 100 mL Erlenmeyer flasks, and 50 mL of isopropanol as the extraction solvent was added thereto and well shaken. Then, the contents in the flask were extracted after allowing them at room temperature for at least 8 hours. Upon extraction, the extract was filtered and concentrated under reduced pressure, and the concentrates in the three Erlenmeyer flasks were collected in a scintillation vial and completely concentrated using a nitrogen gas. A COPD mouse model was prepared by anesthetizing the animal with 7% chloral hydrate followed by allowing them to inhale the mixture of (LPS+CS) [LPS (100 µg/mL) and a standard cigarette extract (cigarette smoking; CS; 4 mg/mL) is mixed in a 1:1 ratio] in an amount of 100 µL through the nose once a week for 3 weeks. Specifically, after weakly anesthetizing a mouse, when there was no movement, the front teeth were immobilized using a rubber band and the mixture of (LPS+CS; 50 µL each to a total amount of 100 µL) was allowed to inhale via through the nose.

The experimental group was divided into (i) a normal group without any treatment (NC); (ii) a control group treated with (LPS+CS), (COPD); and (iii) an experimental group orally administered with *P. weinmannifolia* (30 mg/kg) one hour before the treatment with (LPS+CS) (*P. weinmannifolia*). Upon completion of the experiment, blood, lung lavage fluid, and lung tissue were isolated from the mice of each group.

4-2. Measurement of Total Granular Materials

The Cambridge filter having the cigarette smoke condensates collected thereon was separated from a cigarette holder and placed in each of 100 mL Erlenmeyer flasks, and 50 mL of isopropanol as the extraction solvent was added thereto and well shaken. Then, the contents in the flask were extracted after allowing them at room temperature for at least 8 hours. Upon extraction, the extract was filtered and concentrated under reduced pressure, and the concentrates in the three Erlenmeyer flasks were collected in a scintillation vial and completely concentrated using a nitrogen gas. The TPM (total particulate matter) content in the standard cigarette was calculated using Equation 2 below.

$$TPM(mg/cig) = \frac{W_{FHA} - W_{FHB}}{N} \quad \text{[Equation 2]}$$

In Equation 2 above, TPM represents total particulate matter, $W_{FHA}$ represents the weight of the filter holder after smoking; WFHB represents the weight of the filter holder before smoking; and N represents the number of cigarettes smoked per trap (cig.).

Example 5. Effect of Inhibiting the Production of Inflammatory Cells in the Bronchoalveolar Lavage Fluid To measure the secretion of bronchoalveolar lavage fluid and the total cell number by a *Pistacia weinmannifolia* extract, the mouse bronchi were treated with ACK (8.3 g $NH_4Cl$, 1 g $KHCO_3$ in 1 L demineralized water+0.1 mM EDTA) solution at 37° C. for 5 minutes to lyse red blood cells, again washed with FBS-free/DMEM medium, and stained with 0.04% trypan blue, and the total number of cells was counted.

Specifically, after the blood collection, the mice were dissected. For the isolation of cells from the bronchoalveolar lavage fluid (BALF), a syringe containing 1 mL of FBS-free DMEM medium was injected into the trachea and fixed with a string, and then cells were separated by performing circulation three times and were treated with ACK solution at 37° C. for 5 minutes to lyse red blood cells. Then, the cells were washed with FBS-free DMEM medium, stained again with 0.04% trypan blue, and the total number of cells was counted. In particular, the total extract by methanol obtained in Preparation Example 1 was used.

Table 5 below shows the results of the effect of the methanol extract of *Pistacia weinmannifolia* (total) on the production of neutrophils, among the total inflammatory cells in the bronchoalveolar lavage fluid in the COPD animal model induced with a standard cigarette extract.

NC: normal control without airway sensitization;

COPD induction: COPD-induced group with a standard cigarette;

COPD Induction after treatment with a *Pistacia weinmannifolia* extract: an experimental group administered with a methanol extract of *Pistacia weinmannifolia*.

TABLE 5

| Group | Number of Immune Cells | | | |
|---|---|---|---|---|
| | Total Cells | Inhibition Rate (%) | Neutrophils | Inhibition Rate (%) |
| NC | 20.1 ± 4.41 | — | 0.5 ± 0.12 | — |
| COPD Induction | 95.4 ± 16.99 | — | 202.8 ± 24.48 | — |
| COPD Induction after Treatment with *Pistacia weinmannifolia* Extract | 28.0 ± 5.50 | 70.6 | 116.8 ± 37.43 | 59.8 |

As can be confirmed in Table 5 above, the animal model treated with the standard cigarette extract after the pretreatment with the *Pistacia weinmannifolia* methanol extract of the present invention showed a decrease in the total number of inflammatory cells within the bronchoalveolar lavage fluid and in the number of neutrophils among the inflammatory cells, whereas the animal model treated with the standard cigarette extract showed a rapid increase in the number of neutrophils. In particular, it was confirmed that the pretreatment with a methanol extract significantly reduced the total number of inflammatory cells (70.6%, $P<0.05$) and the amount of neutrophil production (59.8%, $P<0.05$).

Example 6. Effect of Inhibiting the Number of $CD^{4+}$ Cells and Neutrophils Gr-$1^+$ Cells in the Bronchoalveolar Lavage Fluid The BAL cells isolated in Example 5 were adjusted to $5\times10^5$ cells and subjected to immunofluorescence staining at 4° C. PE-anti-CD4 (553047, BD Pharmingen) and PE-anti-Gr-1 (553128, BD Pharmingen) were added to the cells, respectively, and reacted on ice for 30 minutes. After the reaction, the cells were washed at least 3 times with phosphate-buffered saline, and the frequency of $CD^{4+}$ cells and neutrophils Gr-$1^+$ was analyzed as a percentage using the Cell Quest program (643274, BD Pharmingen) of a flow cytometer. Then, the absolute number of cells in each tissue was calculated based on total cells by applying the total number of cells.

Table 6 below shows the measurement results of the effects of a methanol extract of *Pistacia weinmannifolia* on the number of the $CD^{4+}$ cells and neutrophils Gr-$1^+$ within the bronchoalveolar lavage fluid in the COPD-induced animal model.

NC: normal control without airway sensitization;

COPD induction: COPD-induced group with a standard cigarette;

COPD Induction after treatment with a *Pistacia weinmannifolia* extract: an experimental group administered with a methanol extract of *Pistacia weinmannifolia*.

TABLE 6

| Group | Number of Cells | | | |
|---|---|---|---|---|
| | $CD4^+$ Cells $(10^4)$ | Inhibition Rate (%) | Neutrophils Gr-$1^+$ $(10^4)$ | Inhibition Rate (%) |
| NC | 7.5 ± 1.49 | — | 0.4 ± 0.08 | — |
| COPD Induction | 510.1 ± 157.65 | — | 33.9 ± 8.19 | — |
| COPD Induction after Treatment with *Pistacia weinmannifolia* Extract | 152.8 ± 66.25 | 70.3 | 4.7 ± 1.14 | 86.2 |

As can be confirmed in Table 6 above, the COPD-induced group showed a significant increase both in the number of $CD^{4+}$ cells and neutrophils Gr-$1^+$ compared to the normal control. In contrast, the group administered with a *Pistacia weinmannifolia* extract (30 mg/kg) showed an inhibition in the number of $CD^{4+}$ cells compared to the COPD-induced group by 70.3% ($P<0.05$), and also an inhibition in the number of neutrophils Gr-$1^+$ by 86.7% ($P<0.05$).

Example 7. Effect of Inhibiting CXCL-1, TNF-α, and MCP-2 in the Bronchoalveolar Lavage Fluid The levels of CXCL-1, TNF-α, and MCP-2 in the bronchoalveolar lavage (BALF) isolated from the mice were measured by an enzyme-linked immunosorbent assay (ELISA). An antibody specific for each of CXCL-1, TNF-α, and MCP-2 was diluted in coating buffer (291195, R&D System), coated on microwells, and incubated at 4° C. overnight. Each well was washed 3 times with washing buffer, and then 100 μL of serum (10-fold diluted) was aliquoted to each well. Each well was placed at room temperature for 1 hour, washed twice with washing buffer, and each well was treated with 100 μL of avidin-conjugated HRP (DY998, R&D System) placed at room temperature for 1 hour, and washed. The TMB substrate in an amount of 100 μL was added to each well, placed in a dark room for 30 minutes, and treated with 50 μL of a stop solution. Then, the absorbance was measured at 450 nm using an ELISA reader (Emax, Molecular Devices).

Table 7 below shows the measurement results of the effect of a methanol extract of *Pistacia weinmannifolia* on the production of CXCL-1 within the bronchoalveolar lavage fluid in the COPD-induced animal model.

NC: normal control without airway sensitization;

COPD induction: COPD-induced group with a standard cigarette;

COPD Induction after treatment with a *Pistacia weinmannifolia* extract: an experimental group administered with a methanol extract of *Pistacia weinmannifolia*.

TABLE 7

| Group | CXCL-1 (pg/mL) | Inhibition Rate (%) |
|---|---|---|
| NC | 71.9 ± 15.93 | — |
| COPD Induction | 312.6 ± 63.16 | — |
| COPD Induction after Treatment with *Pistacia weinmannifolia* Extract | 103.2 ± 11.06 | 67.0 |

As can be confirmed in Table 7 above, the COPD-induced group showed a significant increase in the production of CXCL-1 within the bronchoalveolar lavage fluid compared to the normal control. In contrast, the group administered with a *Pistacia weinmannifolia* extract (30 mg/kg) showed an inhibition in the production of CXCL-1 compared to the COPD-induced group by 67.0% (P<0.05).

Additionally, Table 8 below shows the measurement results of the effect of a methanol extract of *Pistacia weinmannifolia* on TNF-α, which is an inflammatory factor, in a COPD-induced animal model.

NC: normal control without airway sensitization;
COPD induction: COPD-induced group with a standard cigarette;
COPD Induction after treatment with a *Pistacia weinmannifolia* extract: an experimental group administered with a methanol extract of *Pistacia weinmannifolia*.

TABLE 8

| Group | TNF-α (pg/mL) | Inhibition Rate (%) |
|---|---|---|
| NC | 1.5 ± 0.34 | — |
| COPD Induction | 35.0 ± 9.68 | — |
| COPD Induction after Treatment with *P. weinmannifolia* Extract | 13.0 ± 3.50 | 62.8 |

As can be confirmed in Table 8 above, the COPD-induced group showed a significant increase in the production of TNF-α within the bronchoalveolar lavage fluid compared to the normal control. In contrast, the group administered with a drug, i.e., the group administered with a *Pistacia weinmannifolia* extract (30 mg/kg) showed an inhibition in the production of TNF-α compared to the COPD-induced group by 62.8% (P<0.05).

Additionally, Table 9 below shows the results of the effect of a methanol extract of *Pistacia weinmannifolia* on the production of MCP-2 within the bronchoalveolar lavage fluid, observed in a COPD-induced animal model.

NC: normal control without airway sensitization;
COPD induction: COPD-induced group with a standard cigarette;
COPD Induction after treatment with a *Pistacia weinmannifolia* Extract: an experimental group administered with a methanol extract of *Pistacia weinmannifolia*.

TABLE 9

| Group | MCP-2 (pg/mL) | Inhibition Rate (%) |
|---|---|---|
| NC | 12.0 ± 1.75 | — |
| COPD Induction | 48.7 ± 15.02 | — |
| COPD Induction after Treatment with *P. weinmannifolia* Extract | 17.6 ± 4.07 | 62.8 |

As can be confirmed in Table 9 above, the COPD-induced group showed a significant increase in the production of MCP-2 within the bronchoalveolar lavage fluid compared to the normal control. In contrast, the group administered with a drug, i.e., the group administered with a *Pistacia weinmannifolia* extract (30 mg/kg) showed an inhibition in the production of MCP-2 compared to the COPD-induced group by 62.8% (P<0.05).

Additionally, it was confirmed that the *Pistacia weinmannifolia* extract of the present invention generally does not have any cytotoxicity in a concentration capable of inducing the effect of preventing or treating COPD and chronic obstructive bronchitis, chronic bronchiolitis, emphysema, multiple sclerosis, and acute and pulmonary diseases. The results confirm that the *Pistacia weinmannifolia* extract of the present invention is a natural material effective for the treatment of CDPO without inducing any side-effects to the human body, and thus can be used with safety in the prevention, improvement, or treatment of COPD and chronic obstructive bronchitis, chronic bronchiolitis, emphysema, multiple sclerosis, and acute and pulmonary diseases.

Summarizing the foregoing, it was confirmed that the *Pistacia weinmannifolia* extract of the present invention has a high inhibitory effect on COPD and chronic obstructive bronchitis, chronic bronchiolitis, emphysema, multiple sclerosis, and acute and pulmonary diseases.

Formulation Examples for the composition of the present invention are provided herein below.

Formulation Example 1. Preparation of a Pharmaceutical Formulation

The pharmaceutical formulation of the present invention containing a *Pistacia weinmannifolia* extract or a fraction thereof was prepared according to the conventional method as follows.

Preparation of Powders
a *Pistacia weinmannifolia* extract or a fraction thereof (2 g); or
a compound pistachalcone (PW12) or pistachalcone B (PW13) (0.002 g to 2 g; 0.01 wt % to 10 wt %) prepared in Examples 1-1, 1-2, and 1-3, respectively
lactose (1 g)

The above components were mixed and filled into a sealed pouch to prepare powders.

Preparation of Tablets
a *Pistacia weinmannifolia* extract or a fraction thereof (100 mg); or
a compound pistachalcone (PW12) or pistachalcone B (PW13) (0.1 mg to 100 mg; 0.01 wt % to 10 wt %) prepared in Examples 1-1, 1-2, and 1-3, respectively
corn starch (100 mg)
lactose (100 mg)
magnesium stearate (2 mg)

The above components were mixed and tableted to prepare tablets.

Preparation of Capsules a *Pistacia weinmannifolia* extract or a fraction thereof (100 mg); or a compound pistachalcone (PW12) or pistachalcone B (PW13) (0.1 mg to 100 mg; 0.01 wt % to 10 wt %) prepared in Examples 1-1, 1-2, and 1-3, respectively corn starch (100 mg)

lactose (100 mg)

magnesium stearate (2 mg)

The above components were mixed and filled into gelatin capsules according to the conventional capsule preparation method to prepare capsules.

Preparation of Pills a *Pistacia weinmannifolia* extract or a fraction thereof (1 g); or a compound pistachalcone (PW12) or pistachalcone B (PW13) (0.1 mg to 100 mg; 0.01 wt % to 10 wt %) prepared in Examples 1-1, 1-2, and 1-3, respectively lactose (1.5 g)

glycerin (1 g)

xylitol (0.5 g)

The above components were mixed and prepared into pills according to the conventional method (4 g/pill).

Preparation of Granules a *Pistacia weinmannifolia* extract or a fraction thereof (150 mg); or a compound pistachalcone (PW12) or pistachalcone B (PW13) (0.1 mg to 100 mg; 0.01 wt % to 10 wt %) prepared in Examples 1-1, 1-2, and 1-3, respectively soybean extract (50 mg)

glucose (200 mg)

starch (600 mg)

The above components were mixed, treated with 30% ethanol (100 mg), dried at 60° C. to form granules, and filled into pouches.

Formulation Example 2. Preparation of a Food Composition or Foods 2-1. Preparation of Flour Foods A *Pistacia weinmannifolia* extract or a fraction thereof (0.5 wt % to 5.0 wt %); or a compound pistachalcone (PW12) or pistachalcone B (PW13) (0.01 wt % to 10 wt %) prepared in Examples 1-1, 1-2, and 1-3, respectively, were added into flour. The mixture was used to prepare breads, cakes, cookies, crackers, and noodles, thereby preparing foods for preventing or improving chronic obstructive pulmonary diseases.

2-2. Preparation of Dairy Products

A *Pistacia weinmannifolia* extract or a fraction thereof (5 wt % to 10.0 wt %); or a compound pistachalcone (PW12) or pistachalcone B (PW13) (0.01 wt % to 10 wt %) prepared in Examples 1-1, 1-2, and 1-3, respectively, were added into milk, which was used various dairy products such as butter and ice creams.

2-3. Preparation of Dry Cereal

Unpolished rice, barley, glutinous rice, and adlay, which were dried after alpharization by a known method, were roasted and then prepared into powders with a particle size of 60 mesh using a pulverizer. Black beans, black sesame, and perilla seeds, which were also steamed and dried by a known method, were roasted into powders with a particle size of 60 mesh using a pulverizer. The *Pistacia weinmannifolia* extract, a fraction thereof, or a compound solution isolated therefrom, prepared in Examples 1-1, 1-2, and 1-3, respectively, were concentrated under reduced pressure in a vacuum evaporator, sprayed, and dried using a hot-air drier. The thus-obtained dried product was pulverized to a particle size of 60 mesh using a pulverizer, thereby obtaining dried powders.

The grains, seeds, a *Pistacia weinmannifolia* extract, a fraction thereof, or a compound isolated therefrom were mixed in the following ratio to prepare dry cereal.

grains (unpolished rice (30 wt %), adlay (15 wt %), and barley (20 wt %), seeds (perilla seeds (7 wt %), black beans (8 wt %), and black sesame (7 wt %), dry powder of a *Pistacia weinmannifolia* extract, a fraction thereof (3 wt %); or a compound pistachalcone (PW12) or pistachalcone B (PW13) (1 wt %), lingzhi mushroom (0.5 wt %),

*Rehmannia* root (0.5 wt %)

Formulation Example 3. Preparation of Beverages 3-1. Preparation of Health Beverages a *Pistacia weinmannifolia* extract or a fraction thereof (1,000 mg); or a compound pistachalcone (PW12) or pistachalcone B (PW13) (1 mg to 1,000 mg; 0.01 wt % to 10 wt %) prepared in Examples 1-1, 1-2, and 1-3, respectively citric acid (1000 mg)

oligosaccharide (100 g)

plum concentrate (2 g)

taurine (1 g)

distilled water to a final volume of 900 mL

According to the method for preparing the conventional health beverages, the above ingredients were mixed, heated at 85° C. for about 1 hour while stirring, and the resulting solution was filtered and collected in a 2 L container. The container was sealed, sterilized, and stored in a refrigerator to be used in preparing compositions for the health beverages of the present invention.

The composition ratio above was provided as a preferred embodiment with respect to the relatively suitable ingredients for favored beverages. However, the mixing ratio may be modified randomly according to the regional and national preferences such as demanding social classes, demanding nations, purpose of uses.

3-2. Preparation of Vegetable Juices

A *Pistacia weinmannifolia* extract or a fraction thereof (5 g); or a compound pistachalcone (PW12) or pistachalcone B (PW13) (0.05 g to 5 g) prepared in Examples 1-1, 1-2, and 1-3, respectively, were added into a tomato or carrot juice (1,000 mL) to prepare a vegetable juice for health improvement.

3-3. Preparation of Fruit Juices

A *Pistacia weinmannifolia* extract or a fraction thereof (1 g); or a compound pistachalcone (PW12) or pistachalcone B (PW13) (0.01 g to 1 g) prepared in Examples 1-1, 1-2, and 1-3, respectively, were added into an apple or grape juice (1,000 mL) to prepare a fruit juice for health improvement.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A method for treating or improving chronic obstructive pulmonary disease (COPD) comprising administering to a subject in need thereof a composition comprising a *Pistacia weinmannifolia* extract, a fraction thereof, or a compound isolated therefrom as an active ingredient.

2. The method according to claim 1, wherein the compound comprises a compound represented by the following Formula 1 or Formula 2:

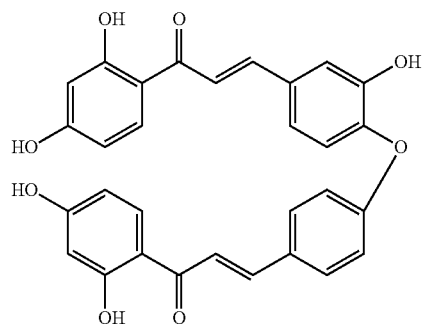

[Formula 1]

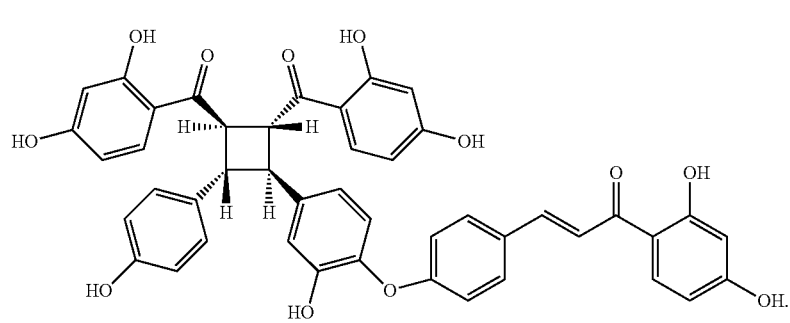

[Formula 2]

3. The method according to claim 1, wherein the extract is obtained by extraction with water, a $C_1$-$C_4$ alcohol, or a mixed solvent thereof.

4. The method according to claim 1, wherein the extract is obtained by extraction with methanol.

5. The method according to claim 1, wherein the fraction is obtained by extraction with water, a $C_1$-$C_4$ alcohol, chloroform, ethyl acetate, hexane, butanol, or a mixed solvent thereof.

6. The method according to claim 1, wherein the chronic obstructive pulmonary disease is at least one selected from the group consisting of chronic obstructive bronchitis, chronic bronchiolitis, emphysema, multiple sclerosis, and acute and chronic inflammation.

7. The method according to claim 1, wherein the extract, the fraction, and the compound have the following activities:
   (a) reducing the number of inflammatory cells around the bronchi or the blood vessels and the number of neutrophils;
   (b) reducing the number of CD4$^+$ cells or neutrophils Gr-1$^+$ cells;
   (c) inhibiting the production of CXCL-1;
   (d) inhibiting the production of TNF-α; or
   (e) inhibiting the production of MCP-2.

8. The method according to claim 1, wherein the composition comprises the *Pistacia weinmannifolia* extract or a fraction thereof in an amount of 1 wt % to 10 wt %; or a compound isolated therefrom in an amount of 0.01 wt % to 10 wt %.

9. The method according to claim 1, wherein the composition comprises a food comprising a *Pistacia weinmannifolia* extract, a fraction thereof, or a compound isolated therefrom.

10. The method according to claim 9, wherein the food composition is a health functional food.

11. The method according to claim 9, wherein the food composition further comprises a sitologically acceptable carrier.

12. The method according to claim 9, wherein the extract is obtained by extraction with water, a $C_1$-$C_4$ alcohol, or a mixed solvent thereof.

13. The method according to claim 9, wherein the extract is obtained by extraction with methanol.

14. The method according to claim 9, wherein the fraction is obtained by extraction with water, a $C_1$-$C_4$ alcohol, chloroform, ethyl acetate, hexane, butanol, or a mixed solvent thereof.

15. The method according to claim 9, wherein the compound comprises a compound represented by the following Formula 1 or Formula 2:

[Formula 1]

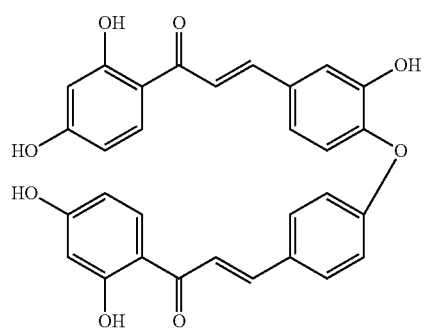

[Formula 2]

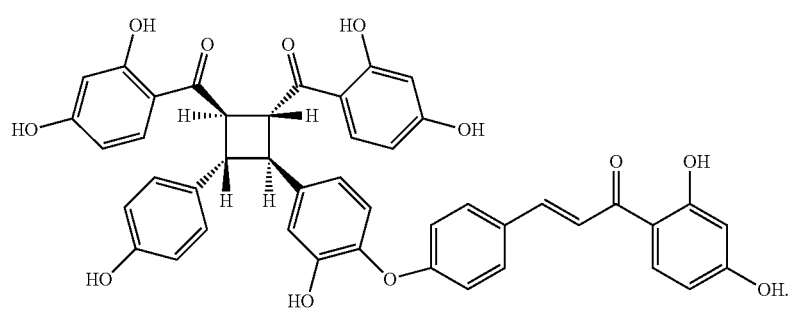

16. The method according to claim 9, wherein the chronic obstructive pulmonary disease is at least one selected from the group consisting of chronic obstructive bronchitis, chronic bronchiolitis, emphysema, multiple sclerosis, and acute and chronic inflammation.

17. The method according to claim 1, wherein the composition comprises a pharmaceutical composition comprising a *Pistacia* weinmannifolia extract, a fraction thereof, or a compound isolated therefrom.

18. The method according to claim 17, wherein the pharmaceutical composition further comprises a pharmaceutically acceptable carrier.

* * * * *